United States Patent
Khosla et al.

(10) Patent No.: US 12,186,002 B2
(45) Date of Patent: Jan. 7, 2025

(54) ORTHOPAEDIC SYSTEMS AND METHODS FOR DEFECT INDICATION

(71) Applicant: ARTHREX, INC., Naples, FL (US)

(72) Inventors: Rudraksh Khosla, Naples, FL (US); Gregory Guederian, Naples, FL (US); John David Paterson, Naples, FL (US)

(73) Assignee: ARTHREX, INC., Naples, FL (US)

( * ) Notice: Subject to any disclaimer, the term of this patent is extended or adjusted under 35 U.S.C. 154(b) by 0 days.

(21) Appl. No.: 18/463,393

(22) Filed: Sep. 8, 2023

(65) Prior Publication Data

US 2023/0414265 A1 Dec. 28, 2023

Related U.S. Application Data

(62) Division of application No. 17/389,407, filed on Jul. 30, 2021, now Pat. No. 11,786,284.

(51) Int. Cl.
| | | |
|---|---|---|
| *A61B 17/17* | (2006.01) | |
| *A61B 17/16* | (2006.01) | |
| *A61B 17/88* | (2006.01) | |
| *A61B 17/90* | (2006.01) | |
| *A61B 90/00* | (2016.01) | |
| *A61B 90/11* | (2016.01) | |
| *A61F 2/46* | (2006.01) | |
| *A61B 17/56* | (2006.01) | |

(52) U.S. Cl.
CPC .......... *A61B 17/90* (2021.08); *A61B 17/1684* (2013.01); *A61B 17/1778* (2016.11); *A61B 17/8897* (2013.01); *A61B 90/11* (2016.02); *A61F 2/4612* (2013.01); *A61B 2017/564* (2013.01); *A61B 2090/0807* (2016.02)

(58) Field of Classification Search
CPC ...... A61B 2090/067; A61B 2090/0807; A61B 17/1778; A61B 17/90; A61B 17/1742; A61B 17/1746; A61B 17/175; A61B 17/1753; A61B 17/8897
See application file for complete search history.

(56) References Cited

U.S. PATENT DOCUMENTS

| | | | |
|---|---|---|---|
| 8,361,076 | B2 | 1/2013 | Roose et al. |
| 8,696,680 | B2 | 4/2014 | Iannotti et al. |
| 8,747,418 | B2 | 6/2014 | Qureshi et al. |
| 8,801,725 | B2 | 8/2014 | Ritter et al. |
| 8,926,627 | B2 | 1/2015 | Iannotti et al. |
| 9,033,990 | B2 | 5/2015 | Iannotti et al. |
| 9,198,732 | B2 | 12/2015 | Iannotti et al. |
| 9,579,107 | B2 | 2/2017 | Schoenefeld |
| 9,717,508 | B2 | 8/2017 | Iannotti et al. |
| 9,741,263 | B2 | 8/2017 | Iannotti et al. |

(Continued)

OTHER PUBLICATIONS

International Search Report and Written Opinion for International Search Report PCT/US2022/038126 mailed Dec. 23, 2022.

(Continued)

*Primary Examiner* — Samuel S Hanna
(74) *Attorney, Agent, or Firm* — Carlson, Gaskey & Olds, P.C.

(57) ABSTRACT

This disclosure relates to surgical devices and methods for repairing bone defects. The defect indicators disclosed herein may be utilized to indicate a precise location of the defect associated with an articular surface of a joint.

20 Claims, 16 Drawing Sheets

(56) References Cited

U.S. PATENT DOCUMENTS

| | | | |
|---|---|---|---|
| 9,826,994 | B2 | 11/2017 | Eash et al. |
| 9,931,168 | B2 | 4/2018 | Brown et al. |
| 10,028,803 | B2 | 7/2018 | O'Neill et al. |
| 10,299,807 | B2 | 5/2019 | Murphy |
| 10,357,378 | B2 | 7/2019 | Borries et al. |
| 10,433,983 | B1 * | 10/2019 | Khosla ................. A61F 2/4612 |
| 10,925,658 | B2 | 2/2021 | Hopkins |
| 11,013,619 | B2 | 5/2021 | Cardon et al. |
| 2013/0245632 | A1 | 9/2013 | Iannotti et al. |
| 2014/0358151 | A1 | 12/2014 | Murphy et al. |
| 2015/0190151 | A1 | 7/2015 | Budhabhatti et al. |
| 2016/0242933 | A1 | 8/2016 | Deransart et al. |
| 2017/0079742 | A1 | 3/2017 | O'Neill et al. |
| 2017/0273806 | A1 | 9/2017 | Cardon et al. |
| 2021/0177441 | A1 | 6/2021 | Madier-Vigneux et al. |

OTHER PUBLICATIONS

International Preliminary Report on Patentability for International Application No. PCT/US2022/038126 mailed Feb. 8, 2024.

* cited by examiner

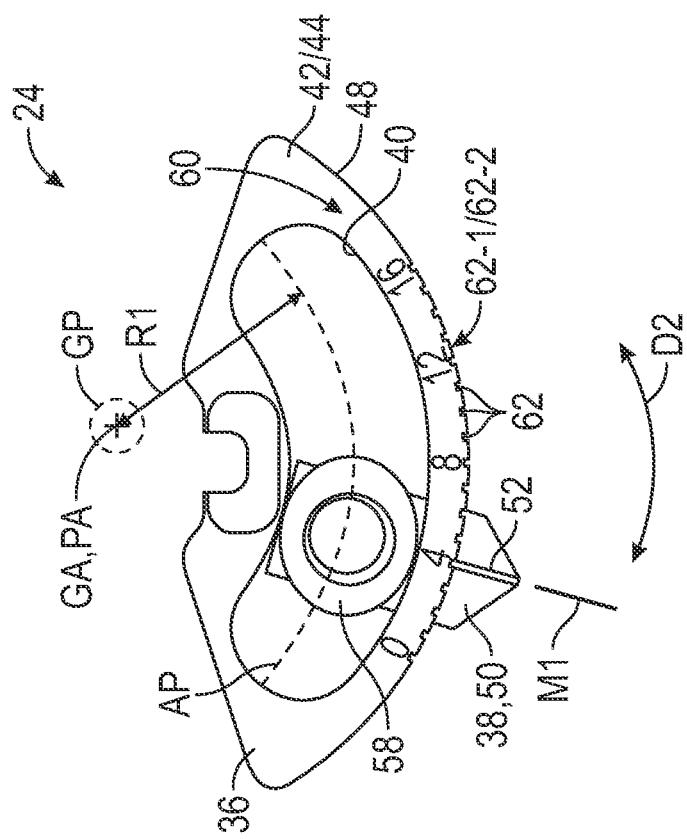
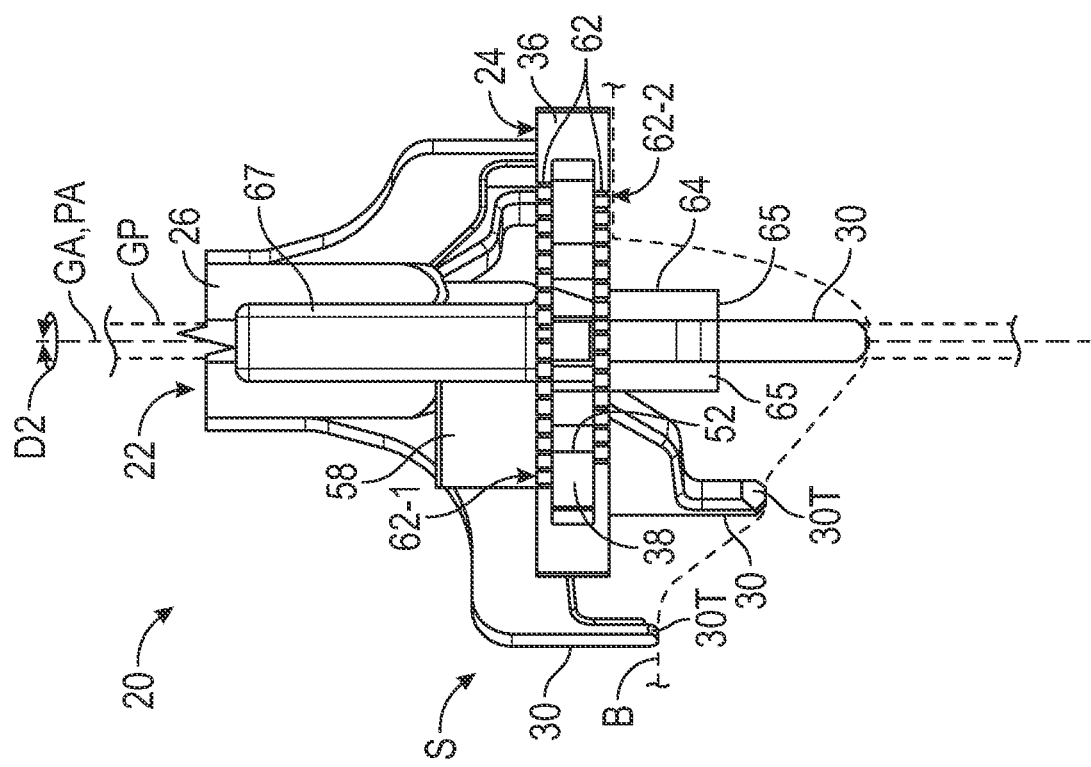
FIG. 9
FIG. 8

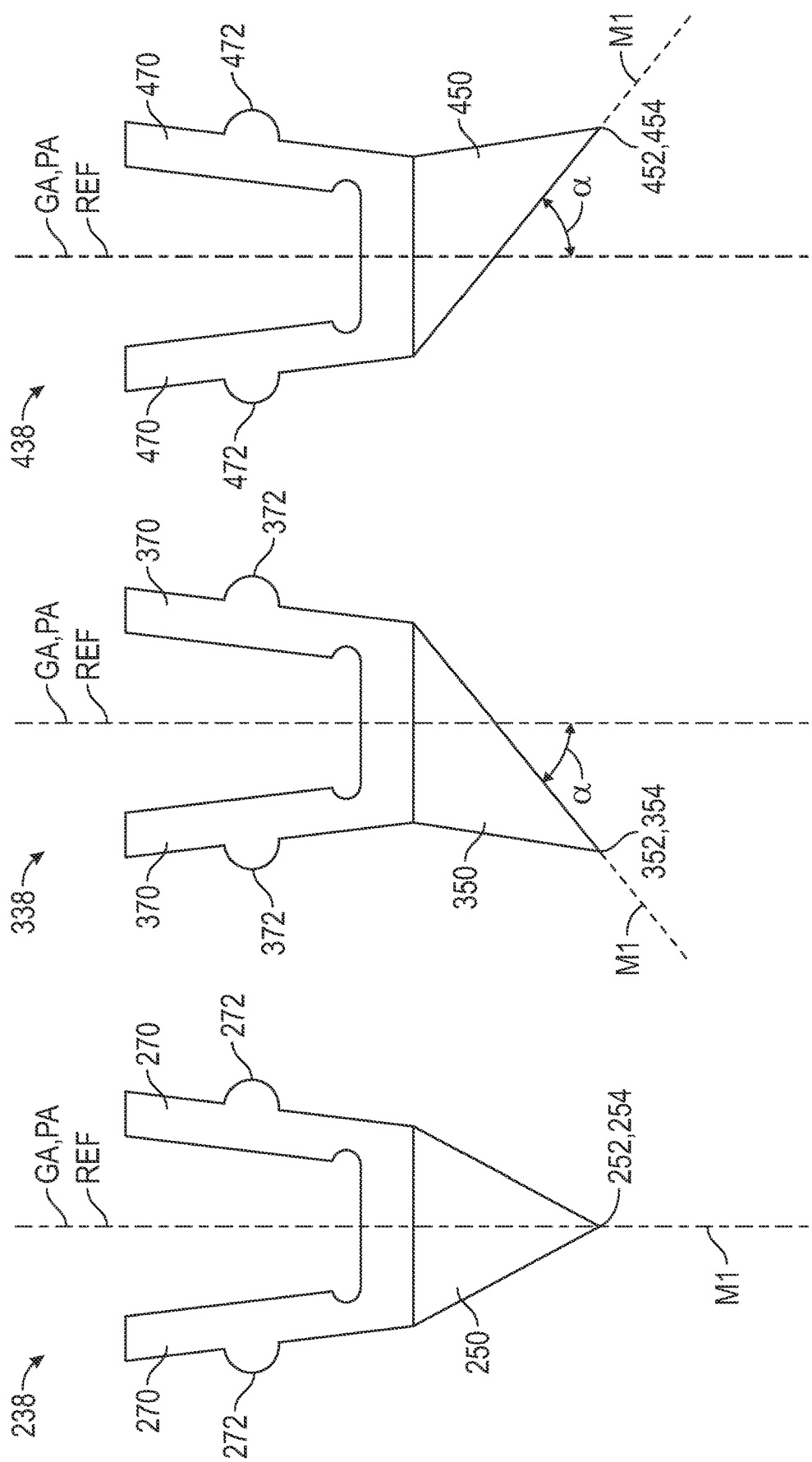

ORTHOPAEDIC SYSTEMS AND METHODS FOR DEFECT INDICATION

CROSS-REFERENCE TO RELATED APPLICATIONS

This application is a divisional of U.S. application Ser. No. 17/389,407 filed Jul. 30, 2021, which is incorporated by reference herein in its entirety.

BACKGROUND

This disclosure relates to surgical devices and methods for repairing bone defects along articular surfaces of a joint.

Many bones of the human musculoskeletal system include articular surfaces. The articular surfaces articulate relative to other bones to facilitate different types and degrees of joint movement. The articular surfaces can erode (e.g., experience bone loss) over time due to repeated use or wear or can fracture as a result of a traumatic impact. These types of bone defects can cause joint instability and pain.

Bone deficiencies may occur along the articular surfaces of the glenoid bone. Some techniques utilize a bone graft and/or implant to fill a defect in the glenoid bone. A reamer may be utilized to form a recess in the bone to remove a portion of the bone defect. The recess may be dimensioned to receive the bone graft or implant.

SUMMARY

This disclosure relates to surgical devices and methods. The surgical device may be used during methods for repairing bone defects. The surgical devices described herein may be utilized to indicate a location along the patient anatomy for forming a recess or otherwise shaping a surface at a surgical site.

An assembly for preparation of a surgical site according to an exemplary aspect of this disclosure may include, inter alia, a trajectory guide that may be configured to set a trajectory of a guide pin relative to bone. The trajectory guide may include a guide body having a passageway that may extend along a longitudinal axis. The passageway may be dimensioned to at least partially receive the guide pin. The assembly may include a defect indicator coupled to the trajectory guide. The defect indicator may include a main body and an indication member coupled to the main body. The indication member may be configured to indicate a direction relative to the longitudinal axis.

A kit for arthroplasty according to an exemplary aspect of this disclosure may include, inter alia, an orthopaedic implant that may be dimensioned to abut bone along a surgical site. The kit may include a trajectory assembly and a reaming assembly. The trajectory guide may include a guide body that may be configured to set a trajectory of a guide pin relative to bone and may include a defect indicator coupled to the trajectory guide. The defect indicator may include an indication member that may be configured to indicate a direction relative to a longitudinal axis of the guide pin. The reaming assembly may include a housing that may be configured to at least partially receive the guide pin to set an orientation of the housing relative to the surgical site. The reaming assembly may include a reaming head that may be rotatable about a reaming axis to remove bone. The reaming axis may be oriented at an oblique angle relative to the assembly axis. The reaming assembly may be moveable such that a distalmost position of the reaming head may be substantially positioned in the direction relative to the longitudinal axis.

A method of installing an orthopaedic implant according to an exemplary aspect of this disclosure may include, inter alia, positioning a trajectory guide in abutment with bone according to a predetermined trajectory. The method may include positioning a guide pin in the bone according to the predetermined trajectory. The method may include position a defect indicator relative to the trajectory guide to indicate a direction relative to a longitudinal axis of the guide pin. The method may include positioning a reaming assembly along the guide pin. The reaming assembly may include a housing and a reaming head coupled to the housing. The reaming head may be oriented at an oblique angle relative to the longitudinal axis of the guide pin. A distalmost position of the reaming head may be substantially positioned in the direction relative to the longitudinal axis. The method may include rotating the reaming head about the guide pin to remove a portion of the bone.

The present disclosure may include any one or more of the individual features disclosed above and/or below alone or in any combination thereof.

The various features and advantages of this disclosure will become apparent to those skilled in the art from the following detailed description. The drawings that accompany the detailed description can be briefly described as follows.

BRIEF DESCRIPTION OF THE DRAWINGS

FIG. 8 illustrates the exemplary trajectory assembly of FIG. 1 situated relative to a surgical site.

FIG. 9 illustrates a plan view of the defect indicator of FIG. 6.

FIG. 15 illustrates a plan view of the indication member of FIG. 13.

FIG. 16 illustrates another exemplary indication member.

FIG. 17 illustrates yet another exemplary indication member.

Like reference numbers and designations in the various drawings indicate like elements.

DETAILED DESCRIPTION

Figure 1:
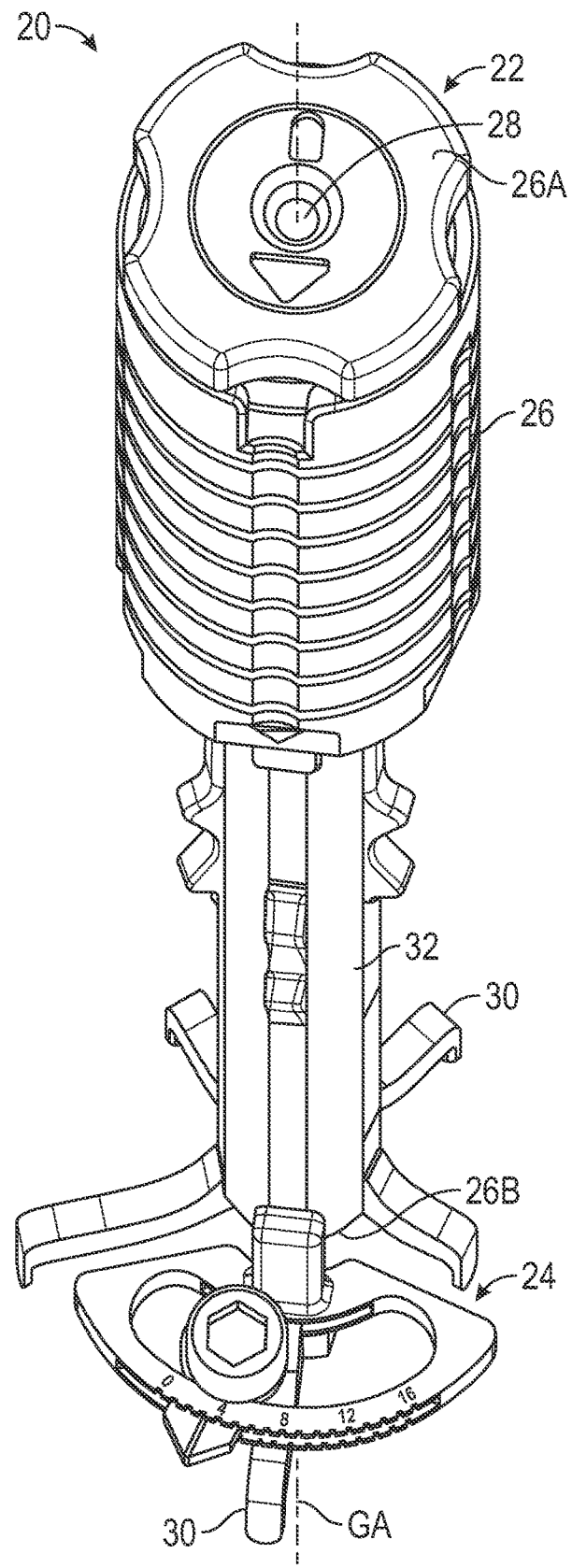
FIG. 1 illustrates a perspective view of an exemplary trajectory assembly including a trajectory guide and defect indicator for preparing a surgical site.

This disclosure relates to surgical devices and methods for repairing bone defects. The instrumentation and systems described herein may be capable of dimensioning or otherwise preparing a defect surface at a surgical site, including reaming bone or other tissue.

The disclosed trajectory assemblies may be utilized to establish a precise trajectory of a guide pin or member and may be utilized to indicate a precise location of a defect relative to the positioned guide pin. The defect may reside along an articular surface of joint. The articular surface may be along a glenoid or another joint. The indicated location may be associated with a localized region of maximum bone defect or bone erosion. The indicated location may be specific to a particular patient and may be utilized to remove at least a portion of bone in the defect region, which may facilitate preservation of bone adjacent to the defect and which may promote healing of the patient. The indicated location may be utilized to form an angled cut along the articular surface.

An assembly for preparation of a surgical site according to an exemplary aspect of this disclosure may include, inter alia, a trajectory guide that may be configured to set a trajectory of a guide pin relative to bone. The trajectory guide may include a guide body having a passageway that may extend along a longitudinal axis. The passageway may be dimensioned to at least partially receive the guide pin. The assembly may include a defect indicator coupled to the trajectory guide. The defect indicator may include a main body and an indication member coupled to the main body. The indication member may be configured to indicate a direction relative to the longitudinal axis.

In a further implementation, the trajectory guide may include at least one arm member dimensioned to abut bone. The at least one arm member may be moveable relative to the guide body to set a position of the at least one arm member relative to the longitudinal axis. The defect indicator may be carried by the at least one arm member.

In a further implementation, at least one arm member may be configured to set the trajectory of the guide pin in response to abutment with the bone.

In a further implementation, the at least one arm member may include a plurality of arm members that may be distributed about a periphery of the guide body.

In a further implementation, each of the arm members may be moveable relative to the guide body to set the trajectory of the guide pin in response to abutment with the bone.

In a further implementation, each of the arm members may include a first portion, a second portion and a third portion. The first portion may be coupled to the guide body. The second portion may extend laterally between the first portion and the third portion. The third portion may establish a terminal end dimensioned to abut bone.

In a further implementation, wherein the bone may be a glenoid.

In a further implementation, the defect indicator may be releasably secured to the at least one arm member.

In a further implementation, the main body may establish a recess. The indication member may include a pointer body that may taper to an apex that may correspond to a predetermined position. The predetermined position may be associated with a bone defect of a patient. The pointer body may be at least partially insertable into the recess such that the apex may be situated relative to the longitudinal axis to indicate the direction.

In a further implementation, the defect indicator may include a carrier releasably secured to the main body. The indication member may include a first portion and a second portion releasably secured to the first portion. The main body may be dimensioned to capture the first portion. The second portion may include a pointer body moveable relative to the carrier. The pointer body may be configured to indicate the direction relative to the longitudinal axis.

In a further implementation, a ruler including indicia may be established along the carrier. The pointer body may be moveable relative to the ruler to indicate a circumferential position relative to the longitudinal axis.

In a further implementation, the indication member may be translatable about the longitudinal axis to set the direction.

In a further implementation, the trajectory guide may include at least one arm member dimensioned to abut bone. The at least one arm member may be moveable relative to the guide body to set a position of the at least one arm member relative to the longitudinal axis.

In a further implementation, the defect indicator may be carried by the at least one arm member.

In a further implementation, the at least one arm member may be configured to set the trajectory of the guide pin in response to abutment with the bone.

In a further implementation, the main body may establishes a first arcuate slot that may be dimensioned to extend about the longitudinal axis. The main body may include a ruler having indicia that may correspond to a set of circumferential positions relative to the longitudinal axis. The indication member may include a pointer body having an indicator aligned with a selected one of the indicia along the ruler in response to translation of the pointer body along the first arcuate slot.

In a further implementation, the defect indicator may include a fastener that may be configured to fix a position of the pointer body in the first arcuate slot.

In a further implementation, the main body may include a second arcuate slot that may be established along a circumferential face. A portion of the pointer body including the indicator may be dimensioned to protrude outwardly from the second arcuate slot.

In a further implementation, the indicia of the ruler may include a first set of indicia and a second set of indicia that may be established along the circumferential face on opposite sides of the second arcuate slot. The first set of indicia may correspond to a first subset of circumferential positions relative to the longitudinal axis. The second set of indicia may correspond to a second subset of circumferential positions relative to the longitudinal axis. The first subset of circumferential positions may circumferentially overlap but may differ from the second subset of circumferential positions to establish the set of circumferential positions.

A kit for arthroplasty according to an exemplary aspect of this disclosure may include, inter alia, an orthopaedic implant that may be dimensioned to abut bone along a surgical site. The kit may include a trajectory assembly and a reaming assembly. The trajectory guide may include a guide body that may be configured to set a trajectory of a guide pin relative to bone and may include a defect indicator coupled to the trajectory guide. The defect indicator may include an indication member that may be configured to indicate a direction relative to a longitudinal axis of the guide pin. The reaming assembly may include a housing that may be configured to at least partially receive the guide pin to set an orientation of the housing relative to the surgical site. The reaming assembly may include a reaming head that may be rotatable about a reaming axis to remove bone. The reaming axis may be oriented at an oblique angle relative to the assembly axis. The reaming assembly may be moveable such that a distalmost position of the reaming head may be substantially positioned in the direction.

In a further implementation, the reaming assembly may include an indicator that may be substantially aligned with the distalmost position of the reaming head relative to the assembly axis. The reaming assembly may be configured such that the indicator may be substantially positioned in the direction in response to rotation of the housing about the guide pin.

A method of installing an orthopaedic implant according to an exemplary aspect of this disclosure may include, inter alia, positioning a trajectory guide in abutment with bone according to a predetermined trajectory. The method may include positioning a guide pin in the bone according to the predetermined trajectory. The method may include position a defect indicator relative to the trajectory guide to indicate a direction relative to a longitudinal axis of the guide pin. The method may include positioning a reaming assembly along the guide pin. The reaming assembly may include a housing and a reaming head coupled to the housing. The reaming head may be oriented at an oblique angle relative to the longitudinal axis of the guide pin. A distalmost position of the reaming head may be substantially positioned in the direction relative to the longitudinal axis. The method may include rotating the reaming head about the guide pin to remove a portion of the bone.

In a further implementation, the method may include forming a first marking along the bone that may be substantially aligned with the direction of the direction of the defect indicator. The step of positioning the reaming assembly may include substantially aligning an indicator along the reaming assembly with the first marking. The indicator may be associated with the distalmost position of the reaming head.

In a further implementation, the method may include securing an implant along the reamed bone subsequent to the rotating step. The implant may be configured to interface with an adjacent bone or an adjacent implant.

In a further implementation, the implant may include a main body portion and a wedge-shaped augment portion that may cooperate to establish a front face and a rear face of the implant. The rear face may be dimensioned to abut the reamed bone.

In a further implementation, the method may include forming a first marking along the bone according to the direction. The method may include substantially aligning a first indicator along the augment portion of the implant with the first marking along the bone prior to the step of securing the implant.

In a further implementation, the step of positioning the reaming assembly may include substantially aligning a second indicator along the reaming assembly with the first marking along the bone. The second indicator may be associated with the distalmost position of the reaming head.

In a further implementation, the trajectory guide may include a guide body and a plurality of arm members distributed about the guide body. The step of positioning the trajectory guide may include moving each of the arm members to respective positions relative to the guide body and into abutment with the bone to establish the predetermined trajectory. The step of positioning the guide pin may include at least partially inserting the guide pin into and through a passageway of the guide body.

In a further implementation, the defect indicator may include a main body and an indication member coupled to the main body. The step of positioning the defect indicator may include moving the indication member relative to the trajectory guide from a first position to a second position to indicate the direction.

In a further implementation, the defect indicator may be carried by one of the arm members.

In a further implementation, the step of moving the indication member relative to the trajectory guide may include moving the indication member relative to the respective one of the arm members.

In a further implementation, the step of rotating the reaming head may include removing the portion of the bone from a glenoid of a patient.

FIGS. 1-5 illustrate an exemplary trajectory assembly 20 that may be utilized for various surgical procedures, including preparation of a surgical site. The trajectory assembly 20 may be utilized in a shoulder reconstruction to facilitate the removal of bone along an articulating surface of a glenoid or humeral head. The bone may be removed from a defect in the articulating surface. A location of the defect may be determined during preoperative planning.

The assembly 20 may include a trajectory guide 22 and a defect indicator 24. The defect indicator 24 may be coupled to the trajectory guide 22. The defect indicator 24 may be utilized to indicate a direction of a bone defect or abnormality relative to the trajectory guide 22. The trajectory guide 22 may be configured to set a trajectory of a guide member relative to bone. Exemplary guide members may include guide pins (e.g., Kirschner wires), as illustrated in FIG. 8 by an elongated guide pin GP positioned at a predetermined trajectory relative to a bone B along a surgical site S (shown in dashed lines for illustrative purposes). The predetermined trajectory may include a location of insertion along a surface of the bone and/or orientation along an axis passing through the location.

Figure 5:
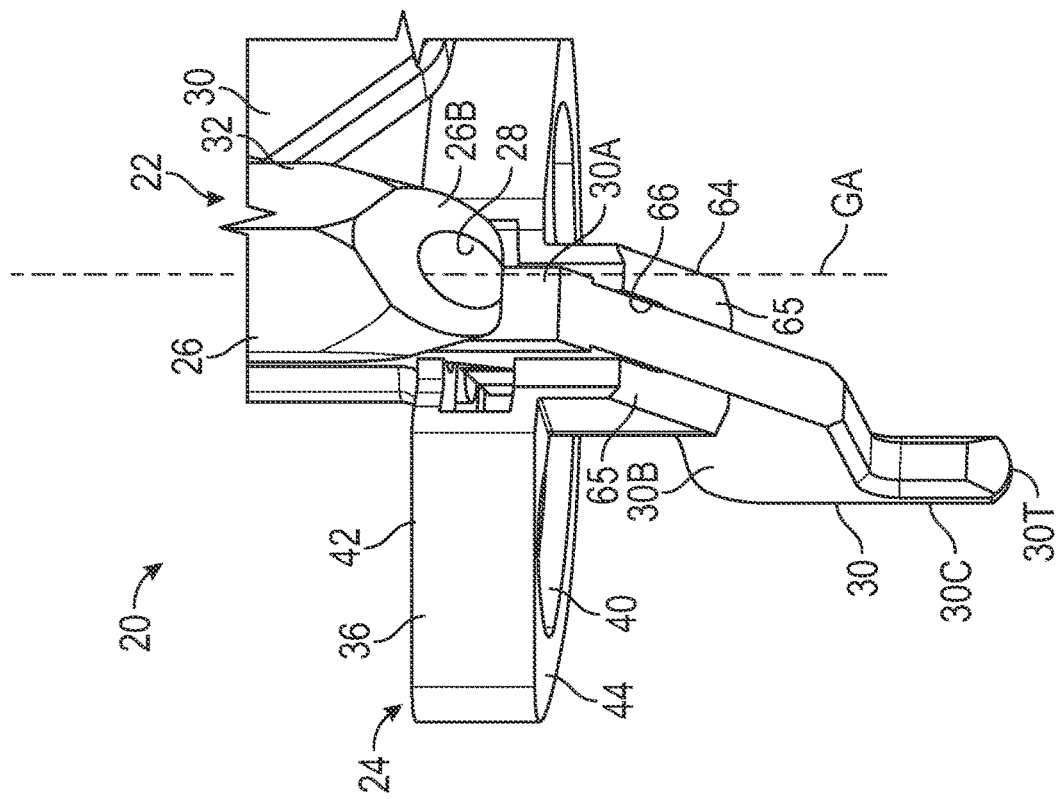
FIG. 5 illustrates another perspective view of the defect indicator of FIG. 2.
Figure 4:
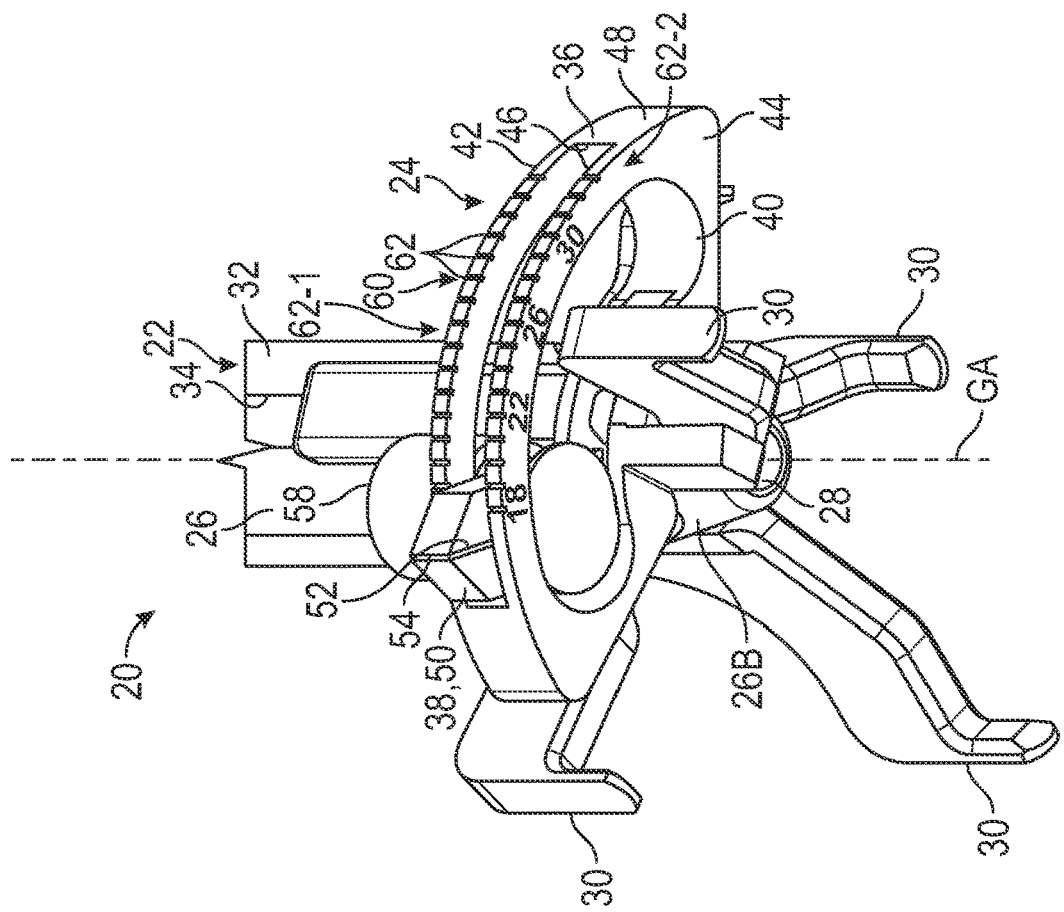
FIG. 4 illustrates another perspective view of the defect indicator of FIG. 2.

The trajectory guide 22 may include an elongated guide body 26 extending along a longitudinal axis GA between a proximal (e.g., first) end portion 26A and a distal (e.g., second) end portion 26B. The guide body 26 may configured to set a trajectory of a guide member relative to tissue such as bone. The guide body 26 may include a passageway 28 that be dimensioned to extend along the longitudinal axis GA (FIGS. 1 and 4-5). The passageway 28 may be dimensioned to at least partially receive the guide member, such as the guide pin GP of FIG. 8.

The trajectory guide 22 may include at least one arm member 30. Each arm member 30 may be configured to orient the longitudinal axis GA of the guide body 26 relative to a contact surface along the surgical site S and establish a trajectory of the guide pin GP, as illustrated in FIG. 8. The contact surface may be established by an articular surface and/or another surface of a bone, such as an articular surface and/or glenoid rim of a glenoid. Each arm member 30 may be dimensioned to abut bone or other tissue along the contact surface. The trajectory guide 22 may include a plurality of the arm members 30 distributed about a periphery 32 and longitudinal axis GA of the guide body 26. Each of the arm members 30 may be configured to set the trajectory of the guide pin GP in response to abutment with the bone or other tissue along the contact surface. Each of the arm members 30 may be attached to the guide body 26 at a fixed position, or may be moveable relative to each other and/or the guide body 26 to set a position of the arm member 30 relative to the longitudinal axis GA. Although a total of five arm members 30 is illustrated in FIGS. 1-5, it should be understood that fewer or more than five arm members 30 may be utilized in accordance with the teachings disclosed herein, such as only one arm member 30. The arm members 30 may be moved to respective positions and fixed relative to the longitudinal axis GA of the trajectory guide 22 prior to, during and/or subsequent to positioning the trajectory guide 22 into abutment with the contact surface. The position of the arm members 30 may be subsequently adjusted by the surgeon or assistant.

Referring to FIGS. 2-5, with continuing reference to FIG. 1, each of the arm members 30 may be movable in a first (e.g., axial) direction D1 (FIG. 2) relative to the guide body 26 to set a trajectory of the guide member relative to tissue such as bone. The direction D1 may be substantially parallel to the longitudinal axis GA. For the purposes of this disclosure, the terms "substantially," "about" and "approximately" mean ±5 percent of the stated value or relationship unless otherwise indicated. Each of the arm members 30 may be independently movable relative to the longitudinal axis GA to set the trajectory of the guide pin relative to the bone or other tissue. Each of the arm members 30 is movable in the direction D1 relative to the longitudinal axis GA of the guide body 26 to set a trajectory of the guide member relative to tissue such as bone. The arm members 30 may set the trajectory in response to abutment with the contact surface along the joint.

Figure 2:
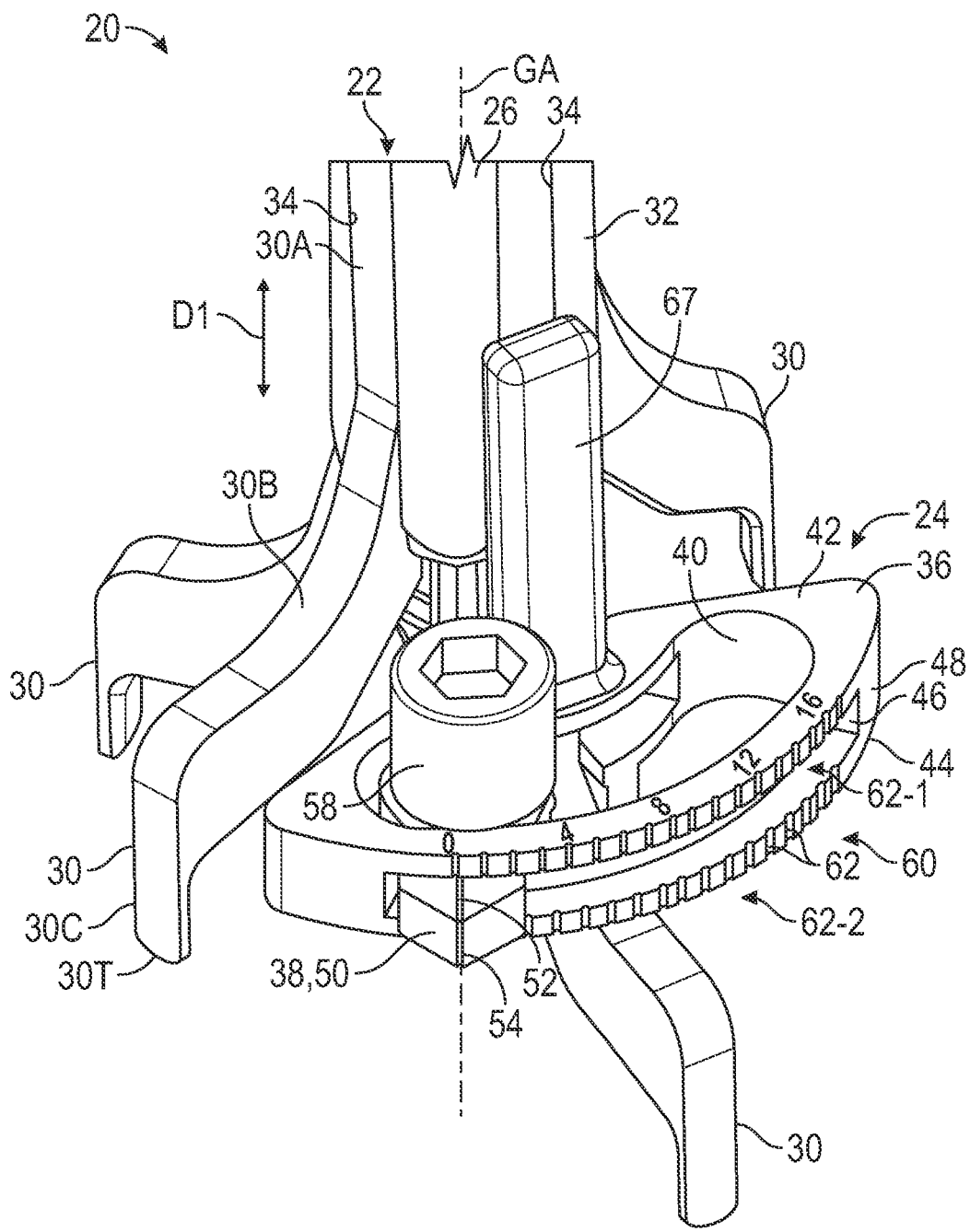
FIG. 2 illustrates a perspective view of the defect indicator coupled to the trajectory guide.
Figure 3:
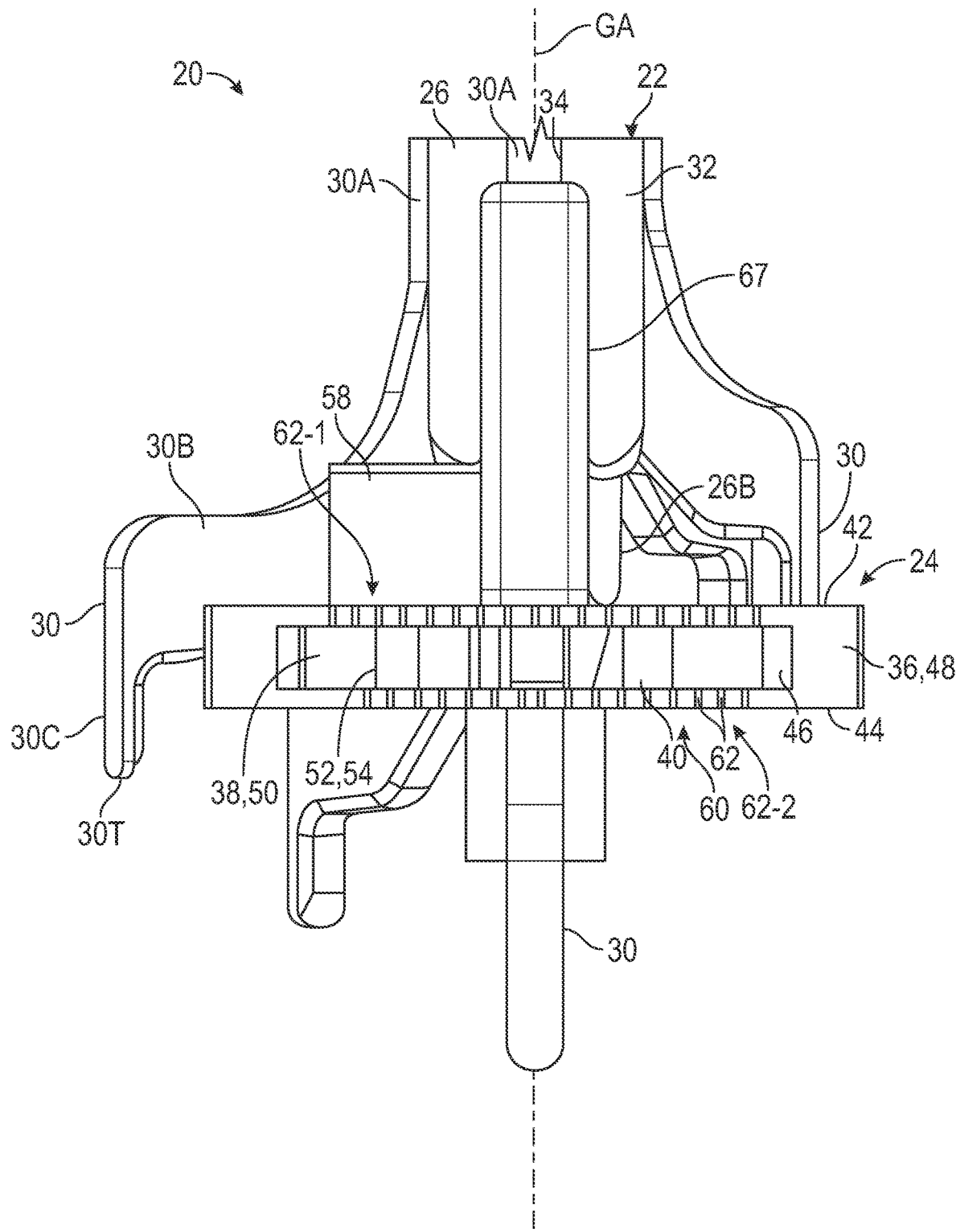
FIG. 3 illustrates a side view of the defect indicator of FIG. 2.

Each of the arm members 30 may include various geometries and configurations to establish a trajectory of the longitudinal axis GA of the guide body 26 and associated guide member(s) relative to the surgical site S. As illustrated in FIGS. 2-3, each of the arm members 30 may include a first portion 30A, a second portion 30B, and a third portion 30C. The first portion 30A may extend proximally from the second portion 30B towards the proximal end portion 26A of the guide body 26 (FIG. 1). The first portion 30A may be coupled to the guide body 26. The first portion 30A may be at least partially captured in a respective slot 34 extending along the periphery 32 of the guide body 26. The second portion 30B may extend laterally between the first portion 30A and the third portion 30C. The second portion 30B may be dimensioned to extend outwardly from the periphery 32 of the guide body 26. The third portion 30C may extend distally from the second portion 30B to establish a terminal end 30T of the respective arm member 30. The terminal end 30T of one or more of the arm members 30 may be established distally of the distal end portion 26B of the guide body 26 (see, e.g., FIG. 3). In other implementations, the second portion 30B may be omitted such that the third portion 30C may extend directly from the first portion 30A to establish the terminal end 30T.

The defect indicator 24 may be carried by at least one of the arm members 30. Movement of the respective arm member 30 relative to the guide body 26 may cause the defect indicator 24 to move relative to the guide body 26 to set a position (e.g., axial position) of the defect indicator 24 relative to the longitudinal axis GA.

The defect indicator 24 may include a main body 36 and an indication member 38 coupled to the main body 36. The main body 36 may be integrally formed with the respective arm member 30 or may be a separate and distinct component. The defect indicator 24 may be releasably secured to the respective arm member 30. The defect indicator 24 may be coupled to another portion of the trajectory guide 22, such as the periphery 32 of the guide body 26 adjacent to the distal end portion 26B.

The indication member 38 may be configured to indicate at least one or more directions relative to the longitudinal axis GA of the trajectory guide 22 and/or a longitudinal axis PA of the guide pin GP (FIGS. 8-9). Each of the directions may be associated with a respective circumferential position about the longitudinal axis GA and/or longitudinal axis PA. The direction and circumferential position may be predetermined and/or adjusted preoperatively and/or intraoperatively. The direction and circumferential position of the defect relative to the trajectory guide 22, as indicated by the indication member 38, and the position and orientation of the selected implant(s) and/or instrumentation(s) may be predetermined preoperatively by evaluating one or more images or models. The preoperative plan may include one or more settings and/or dimensions corresponding to a position of each of the arm members 30 relative to the longitudinal axis GA of the guide body 26. The preoperative plan may include one or more settings and/or dimensions of the defect indicator 24, including positioning of the indication member 38 to indicate a direction and/or location of the defect. One would understand how to establish a suitable preoperative plan for configuration of the trajectory guide 22 and/or defect indicator 24 utilizing the techniques disclosed herein.

Various techniques may be utilized to couple the indication member 38 to the main body 36 of the defect indicator 24. The indication member 38 may be integrally formed with the main body 36 or may be a separate and distinct component. In implementations, the indication member 38 may be integrally formed with the main body 36 at a predetermined direction and circumferential position relative to the longitudinal axis GA of the guide body 26. In the implementation of FIGS. 2-7, the indication member 38 may be movable relative to the main body 36 of the defect indicator 24 to set the circumferential position of the indication member 38 about the longitudinal axis GA of the guide body 26, which may correspond to the predetermined direction associated with a location of a bone defect or abnormality relative to the trajectory guide 22. The indication member 38 may be translatable about the longitudinal axis GA of the guide body 26 to set the circumferential position.

The main body 36 of the defect indicator 24 may establish a first arcuate slot 40 and/or a second arcuate slot 46. The first and second arcuate slots 40, 46 may be dimensioned to extend about the longitudinal axis GA of the guide body 26. The first arcuate slot 40 may be dimensioned to extend at least partially or completely between a proximal (e.g., first) face 42 and a distal (e.g., second) face 44 of the main body 36. The first arcuate slot 40 may be dimensioned to substantially follow a radius. For example, first arcuate slot 40 may extend along an arc path AP established by a radius R1 associated with the longitudinal axis GA, as illustrated in FIG. 9. The first arcuate slot 40 may be span between or may be otherwise associated with a set of circumferential positions relative to the longitudinal axis GA. The set of circumferential positions may correspond to the arc path AP. The first arcuate slot 40 and associated arc path AP may extend at least 15 degrees, or more narrowly between 30 degrees and 90 degrees, about the longitudinal axis GA to establish the set of circumferential positions.

The second arcuate slot 46 may be established along a circumferential face 48. The circumferential face 48 may be dimensioned to extend between the proximal face 42 and distal face 44.

The indication member 38 may be moveable in a second (e.g., circumferential) direction D2 along the first and/or second arcuate slots 40, 46 to select a circumferential position along the arc path AP within the set of circumferential positions, as illustrated in FIG. 9 (see also FIG. 8). The indication member 38 may be configured to indicate a selected (e.g., first) circumferential position relative to a longitudinal (e.g., pin) axis PA of the guide pin GP (shown in dashed lines in FIGS. 8-9 for illustrative purposes).

Figure 7:
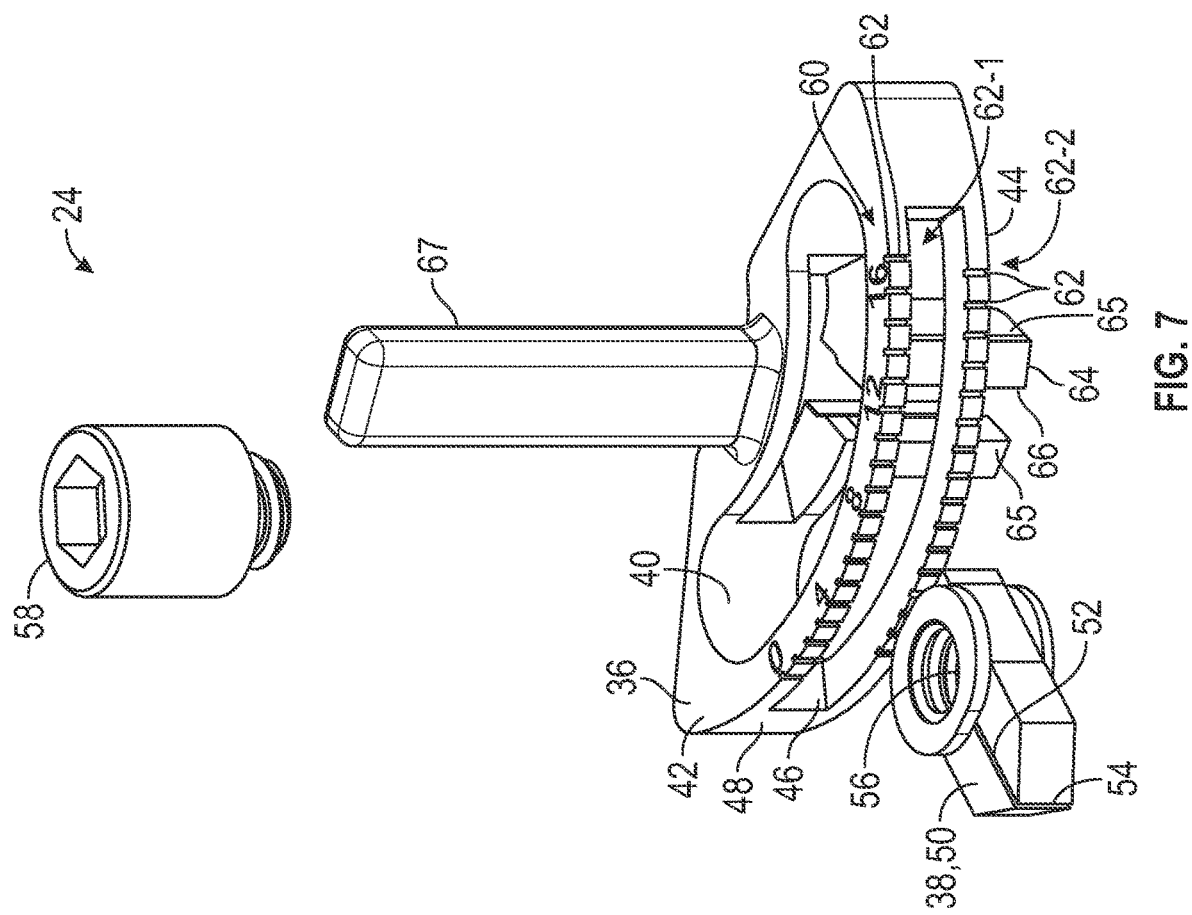
FIG. 7 illustrates an exploded view of the defect indicator of FIG. 6.
Figure 6:
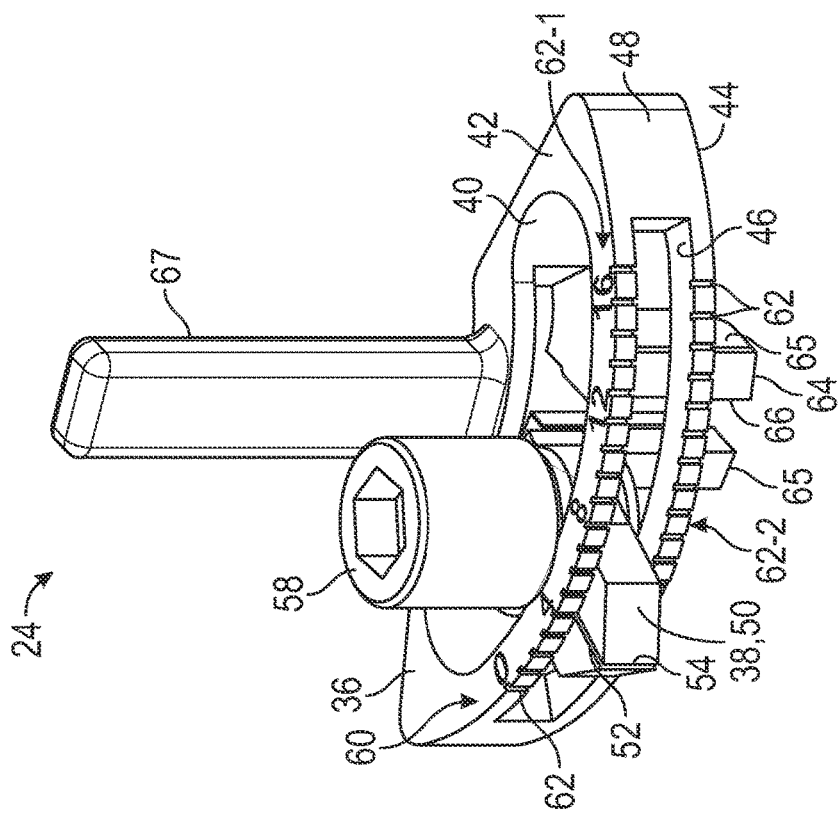
FIG. 6 illustrates an isolated view of the defect indicator of FIG. 2.

Referring to FIGS. 6-7, with continuing reference to FIGS. 1-4, the indication member 38 may incorporate various features to indicate the predetermined or selected circumferential position. The indication member 38 may include a pointer body 50 having an indicator 52. The pointer body 50 may be dimensioned to taper to an apex 54. The indicator 52 may extend along or may otherwise be substantially aligned with the apex 54. A portion of the pointer body 50 including the indicator 52 may be dimensioned to protrude outwardly from the second arcuate slot 46, as illustrated in FIGS. 2, 4, and 6. The indicator 52 may be utilized to indicate the predetermined direction of a bone defect or abnormality relative to the longitudinal axis GA of the trajectory guide 22.

Various techniques may be utilized to secure the indication member 38 to the main body 36 of the defect indicator 24. The defect indicator 24 may include a fastener 58 fixedly attached or otherwise coupled to the indicator member 38. The fastener 58 may be configured to fix a position of the pointer body 50 in the first arcuate slot 40 and/or second arcuate slot 46, as illustrated in FIGS. 2-4 and 6. The fastener 58 may be a thumb screw including threading that mates with threading along an aperture 56 of the pointer body 50 (FIG. 7) to fix the indication member 38 at a selected position relative to the main body 36. In implementations, the fastener 58 is omitted.

The defect indicator 24 may include various features to indicate a position of the indication member 38 relative to the second arcuate slot 46 and/or longitudinal axis GA of the guide body 26. The main body 36 of the defect indicator 24 may include a ruler 60 having indicia 62. The ruler 60 may be established along a surface of the main body 36, such as along the proximal face 42, distal face 44 and/or circumferential face 48. The indicia 62 and indicator 52 may be established utilizing various techniques such as grooves, notches, protrusions and/or other markings along surfaces of the main body 36 and pointer body 50.

The indicia 62 may correspond to a set of circumferential positions relative to the longitudinal axis GA. Each circumferential position may be associated with a respective direction from the longitudinal axis GA. Each of the indicia 62 may include values associated with respective circumferential positions relative to the longitudinal axis GA of the guide body 26. Each value may be associated with a respective degree about the longitudinal axis GA.

The indicator 52 may be configured to be aligned with a selected one of the indicia 62 along the ruler 60 in response to translation of the pointer body 50 in the direction D2 along the first arcuate slot 40 and/or about the longitudinal axis GA of the guide body 26, as illustrated in FIG. 9. The surgeon may form a first marking M1 along tissue such as bone to mark or otherwise indicate the circumferential position and/or direction of the indicator 52. The first marking M1 may be referenced by the surgeon to perform one or more steps of a surgical procedure subsequent to removing the assembly 20 from the surgical site.

The indicia 62 of the ruler 60 may be distributed along the circumferential face 48 proximally and/or distally of the second arcuate slot 46. The indicia 62 may include a first set of indicia 62-1 and a second set of indicia 62-2 spaced apart from the first set of indicia 62-1. The first and second sets of indicia 62-1, 62-2 may be established along the circumferential face 48 on opposite sides of the second arcuate slot 46. The first set of indicia 62-1 may correspond to a first subset of circumferential positions relative to the longitudinal axis GA. The second set of indicia 62-2 may correspond to a second subset of circumferential positions relative to the longitudinal axis GA. The first and second subsets of circumferential positions may be the same or may differ. The first subset of circumferential positions may circumferentially overlap with, but may differ from the second subset of circumferential positions to establish the set of circumferential positions spanning along the ruler 60. Indicia 62 of the first set of indicia 62-1 may be circumferentially interleaved with indicia 62 of the second set of indicia 62-2 relative to the longitudinal axis GA of the trajectory guide 22 such that each of the indicia 62 of the first set of indicia 62-1 is circumferentially offset from each of the indicia 62 of the second set of indicia 62-2. The first and second sets of indicia 62-1, 62-2 may be dimensioned to establish indicia 62 at approximately 1 degree intervals or increments. Adjacent indicia 62 in the respective first and second sets of indicia 62-1, 62-2 may be spaced at intervals between approximately 1 degree and approximately 4 degrees from each other. In implementations, adjacent indicia 62 in the first set of indicia 62-1 may be spaced at approximately 3 degree or approximately 4 degree intervals, and adjacent indicia 62 in the second set of indicia 62-2 may be spaced at approximately 2 degree intervals. Arrangement of the indicia 62 utilizing the techniques disclosed herein may be utilized to more precisely indicate the circumferential position or direction of a bone defect along the articular surface.

The defect indicator 24 may include an interface member 64 dimensioned to extend outwardly from the distal face 44 of the main body 36. The interface member 64 may include a pair of flanges 65 that establish a slot 66. The slot 66 may be dimensioned to establish an interference fit with the second portion 30B or another portion of the respective arm member 30, as illustrated in FIG. 5 (see also FIGS. 6-7). The interface member 64 may be utilized to securely position the defect indicator 24 to a selected one of the arm members 30.

The defect indicator 24 may include a support member 67. The support member 67 may be dimensioned to extend along and abut the periphery 32 of the guide body 26 and/or the first portion 30A of the respective arm member 30, as illustrated in FIGS. 3-4. The support member 67 may serve to improve stability and positioning of the defect indicator 24 relative to the trajectory guide 22.

Figure 10:
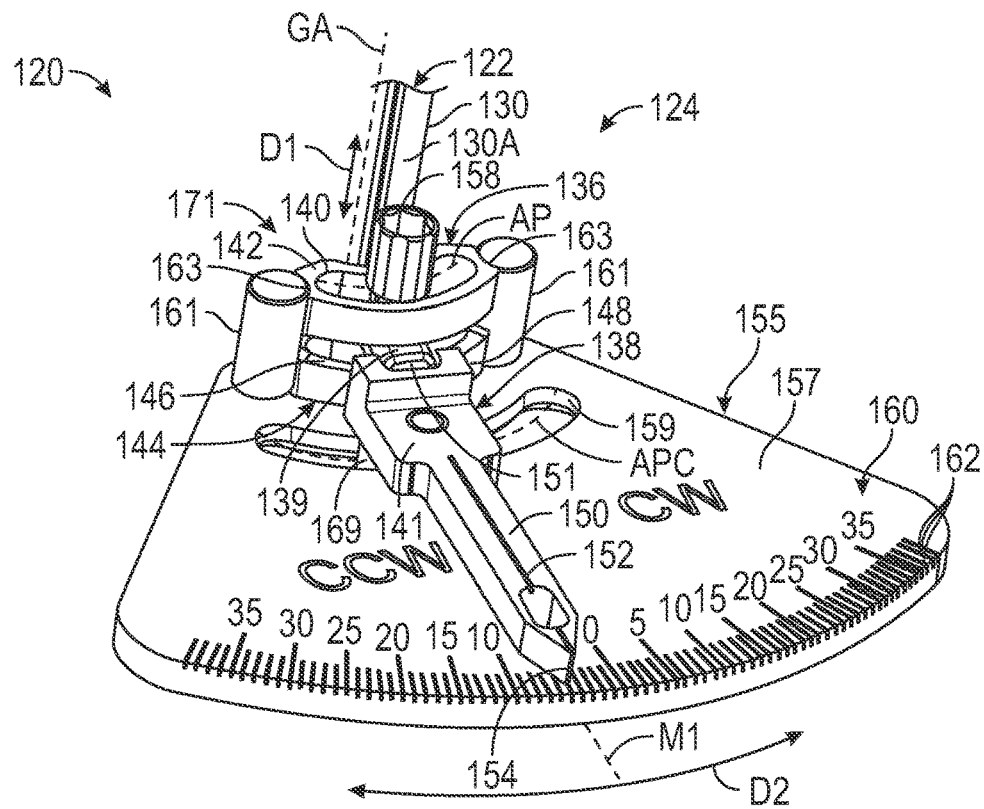
FIG. 10 illustrates a perspective view of another exemplary trajectory assembly including a trajectory guide and defect indicator for preparing a surgical site.
Figure 11:
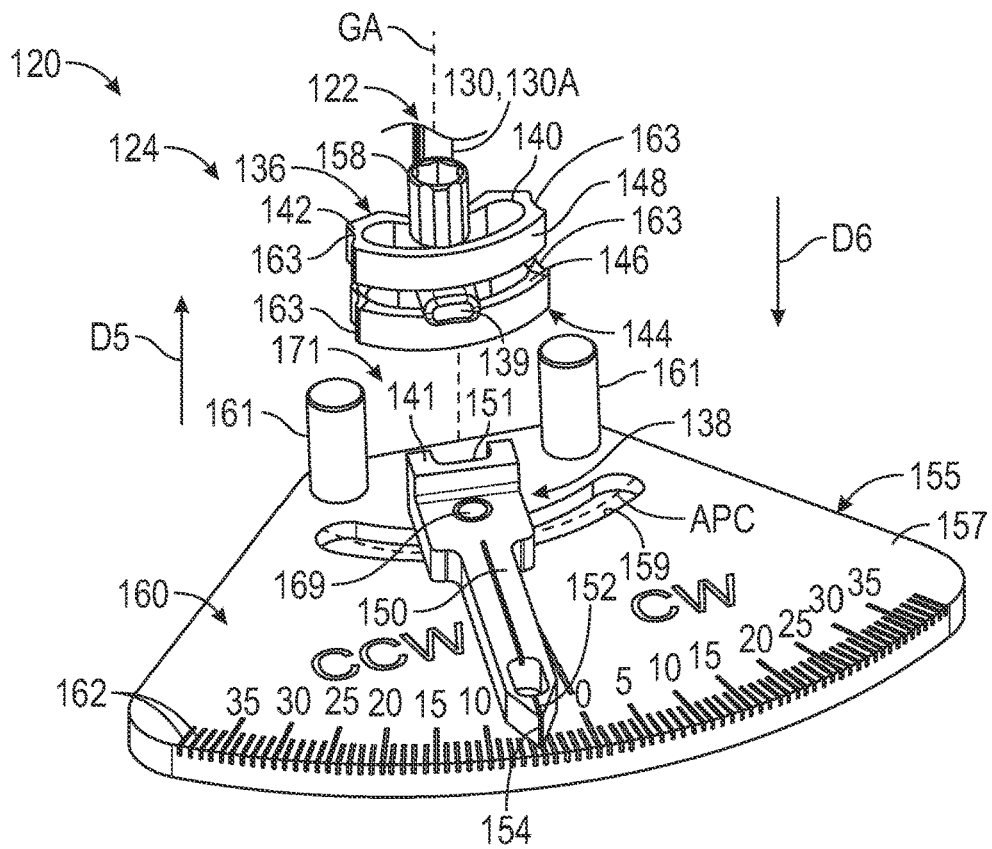
FIG. 11 illustrates a perspective view of the defect indicator including an indication member in an uninstalled position.

FIGS. 10-11 illustrate an exemplary trajectory assembly 120 that may be utilized for preparation of a surgical site. In this disclosure, like reference numerals designate like elements where appropriate and reference numerals with the addition of one-hundred or multiples thereof designate modified elements that are understood to incorporate the same features and benefits of the corresponding original elements.

The trajectory assembly 120 may include a trajectory guide 122 and a defect indicator 124 coupled to the trajectory guide 122. The defect indicator 124 may be releasably secured to an arm member 130 or another portion of the trajectory guide 122. The defect indicator 124 may be carried by the arm member 130. Movement of the arm member 130 relative to a longitudinal axis GA of the trajectory guide 122 may cause the defect indicator 124 to move relative to the guide body (see, e.g., FIG. 2) to set a position (e.g., axial position) of the defect indicator 124 relative to the longitudinal axis GA. The arm member 130 may be movable in a first (e.g., axial) direction D1 (FIG. 10) relative to the longitudinal axis GA. In other implementations, the arm member 130 is fixed relative to the longitudinal axis GA. The defect indicator 124 may be coupled to a first portion 130A of the arm member 130.

The defect indicator 124 may include a main body 136 and an indication member 138 coupled to the main body 136. The main body 136 may be integrally formed with the first portion 130A of the arm member 130 or may be a separate and distinct component. At least a portion of the defect indicator 124 may be releasably secured to the respective arm member 130, including the indication member 138. The indication member 138 may be movable relative to the main body 136 to set a circumferential position of the indication member 138 about the longitudinal axis GA and indicate a direction of a defect relative to the longitudinal axis GA of the trajectory guide 122.

The main body 136 of the defect indicator 124 may establish a first arcuate slot 140 and/or a second arcuate slot 146. The first and second arcuate slots 140, 146 may be dimensioned to extend about the longitudinal axis GA. The slots 140, 146 may be dimensioned according to any of the techniques disclosed herein.

The indication member 138 may include a first (e.g., base) portion 139 and a second (extension) portion 141. The main body 136 may be dimensioned to capture the first portion 139. The first portion 139 may be moveable in a second (e.g., circumferential) direction D2 along the first and/or second arcuate slots 140, 146 to select a circumferential position along an arc path AP within a set of circumferential positions relative to the longitudinal axis GA, as illustrated in FIG. 10. The first portion 139 may be coupled to the main body 136 with a fastener 158. The fastener 158 may be configured to fix a position of the first portion 139 in the first arcuate slot 140 and/or second arcuate slot 146. An end of the first portion 139 may be dimensioned to protrude outwardly from the second arcuate slot 146.

The second portion 141 may be releasably secured or otherwise coupled to the first portion 139. The second portion 141 may establish a pointer body 150. The pointer body 150 may be configured to indicate a direction relative to the longitudinal axis GA of the trajectory guide 122. The pointer body 150 may include a recess 151 dimensioned to receive the end of the first portion 139 that protrudes from the second arcuate slot 146, as illustrated in FIG. 10.

The pointer body 150 may have an indicator 152. The pointer body 150 may be dimensioned to taper to an apex 154. The indicator 152 may extend along or may otherwise be substantially aligned with the apex 154.

The defect indicator 124 may include a carrier 155. The carrier 155 may be releasably secured to the main body 136. The carrier 155 may include a carrier body 157. The carrier body 157 may be substantially planar. The pointer body 150 of the indication member 138 may be secured to the carrier body 157.

The pointer body 150 may be moveable relative to the carrier body 157 of the carrier 155. The carrier body 157 may include a third arcuate slot 159. The third arcuate slot 159 may extend along an arc path APC. The third arcuate slot 159 may span between or may be otherwise associated with a set of circumferential positions relative to the longitudinal axis GA. The set of circumferential positions may correspond to the arc path APC. The arc paths AP, APC may be established by a common radius associated with the longitudinal axis GA (see, e.g., radius R1 of FIG. 9). A guide 169 may be extend from the pointer body 150. The guide 169 may be integrally formed with the pointer body 160 or may be a separate and distinct component coupled to the pointer body 150. The guide 169 may be captured in the third arcuate slot 159 (see FIG. 10) and may be dimensioned to substantially follow the arc path APC to set a position of the pointer body 150. The second portion 149 of the indication member 138 may be moveable in the second direction D2 relative to the third arcuate slot 159 to select a circumferential position along the arc path APC within a set of circumferential positions relative to the longitudinal axis GA, as illustrated in FIG. 10.

A ruler 160 including indicia 162 may be established along the carrier 155. The ruler 160 may be established along a surface of the carrier body 157. The indicia 162 and indicator 152 may be established utilizing any of the techniques disclosed herein. The pointer body 150 may be moveable relative to the ruler 160 to indicate a circumferential position relative to the longitudinal axis GA of the trajectory guide 122. The indicator 152 may be configured to be aligned with a selected one of the indicia 162 along the ruler 160 in response to translation of the pointer body 150 in the direction D2 relative to the third arcuate slot 159 and/or about the longitudinal axis GA, as illustrated in FIG. 10. The surgeon may form a first marking M1 (FIG. 10) along tissue such as bone to mark or otherwise indicate the circumferential position and/or direction of the indicator 152.

Various techniques may be utilized to secure the carrier 155 to the main body 136 of the defect indicator 124. The defect indicator 124 may include one or more supports (e.g., pillars) 161 extending outwardly from the carrier body 157. The supports 161 may have a substantially cylindrical geometry and may be situated adjacent opposed ends of the third arcuate slot 159. Recesses 163 may be established along opposed sidewalls of the main body 136. The recesses 163 may substantially conform to an outer periphery of the supports 161. The supports 161 may be moved in a fifth direction D5 (FIG. 11) and may be at least partially inserted into the respective recesses 163, as illustrated in FIG. 10. The fifth direction D5 may be substantially parallel or transverse to the longitudinal axis GA of the trajectory guide 122. The supports 161 may be spaced apart to establish a gap 171 that at least partially receives the main body 136. The supports 161 may be dimensioned to abut against the main body 136 to secure the carrier 155. The supports 161 and recesses 163 may be dimensioned to establish an interference fit between the main body 136 and supports 161. The supports 161 may be dimensioned to limit movement of the first portion 139 of the indication member 138 relative to the longitudinal axis GA.

The second portion 141 of the indication member 138 may be moved in the fifth direction D5 with the supports 161 such that the end of the first portion 139 is at least partially received in the recess 151 of the second portion 141. To release the carrier 155 from the main body 136, the supports 161 and/or second portion 141 of the indication member 138 may be moved in a sixth direction D6 (FIG. 11), which may substantially oppose the fifth direction D5.

Figure 12:
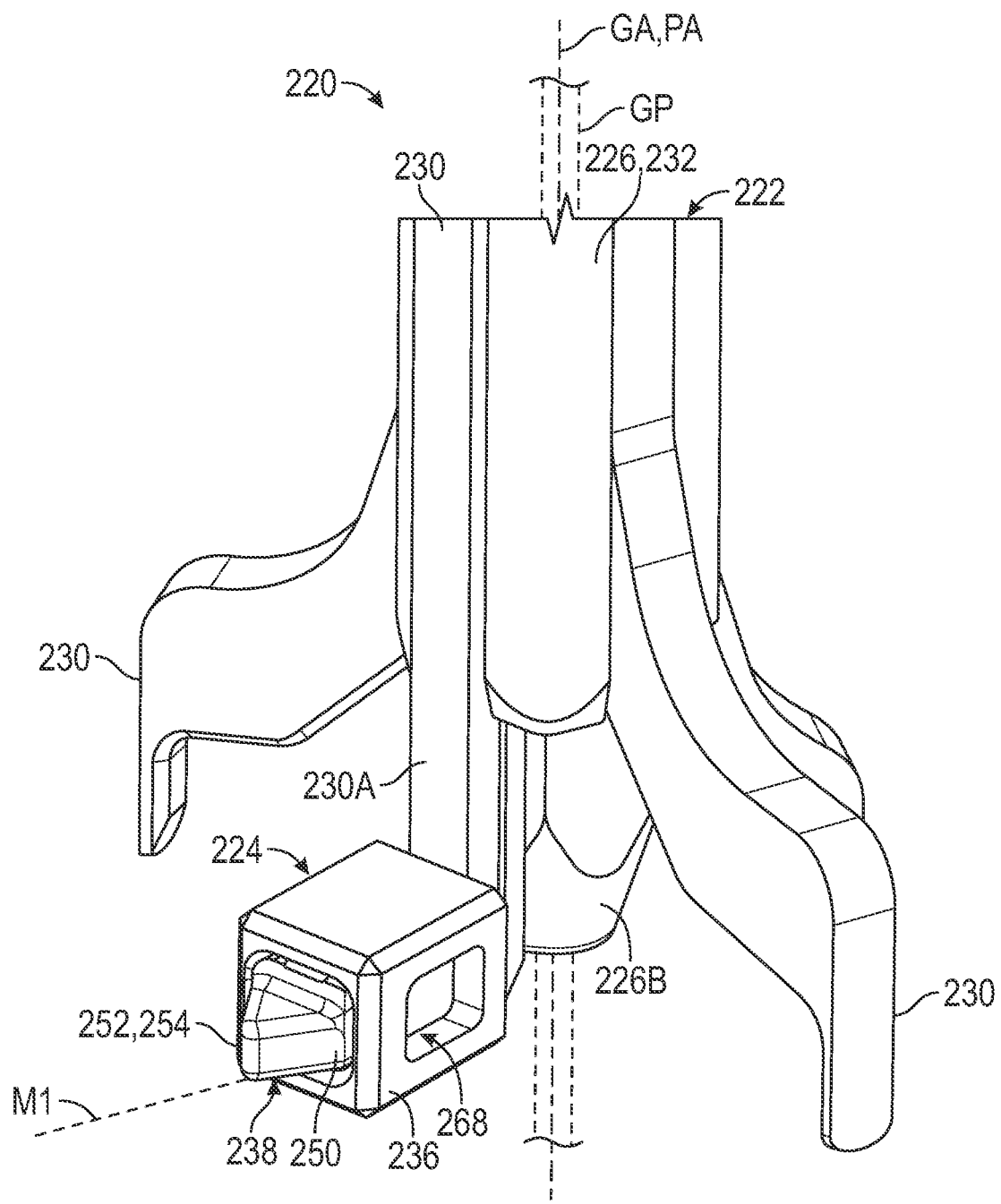
FIG. 12 illustrates a perspective view of another exemplary trajectory assembly including a trajectory guide and defect indicator for preparing a surgical site.
Figure 14:
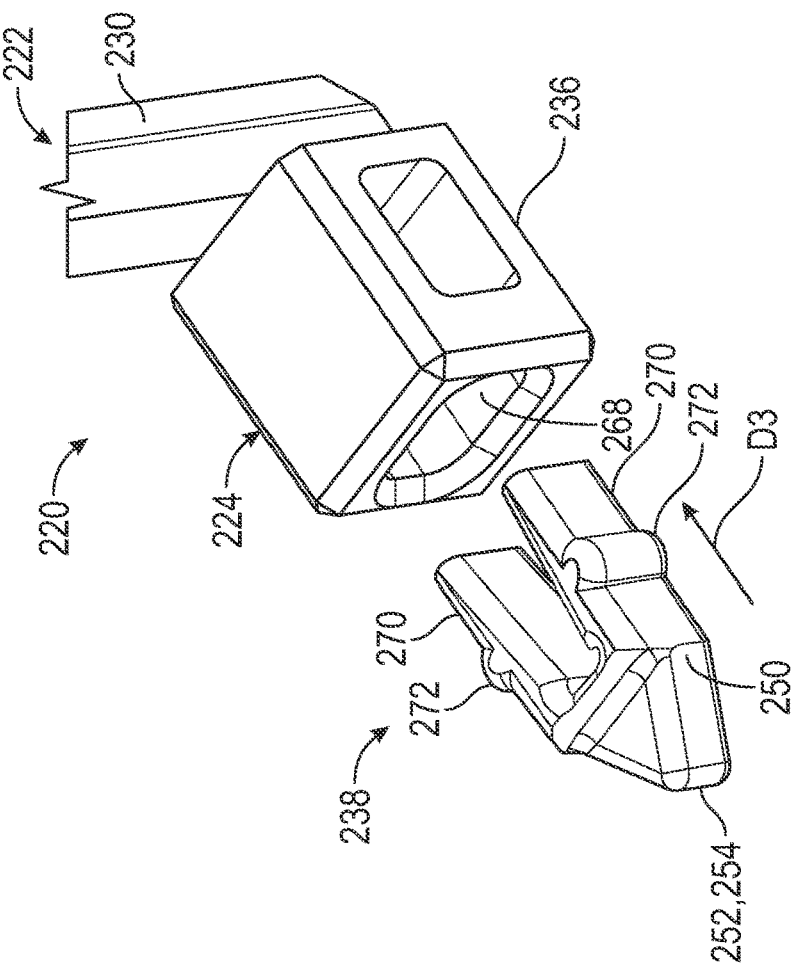
FIG. 14 illustrates perspective view of the defect indicator of FIG. 11 including the indication member in an uninstalled position.
Figure 13:
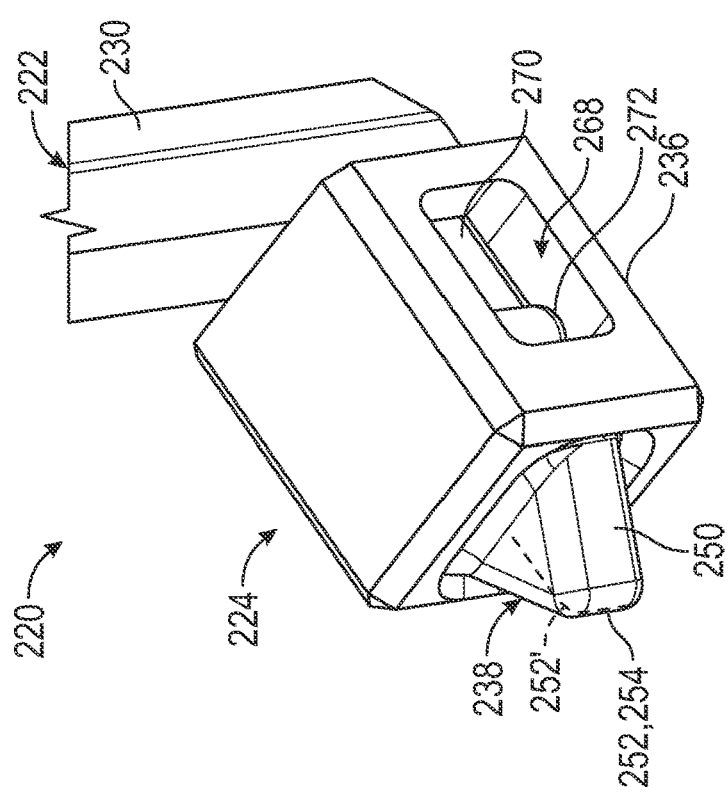
FIG. 13 illustrates a perspective view of the defect indicator including an indication member in an installed position.

FIGS. 12-14 illustrate another exemplary trajectory assembly 220 that may be utilized for preparation of a surgical site. The trajectory assembly 120 may include one or more components dimensioned with respect to an anatomy of a patient. Referring to FIG. 12, the assembly 220 may include a trajectory guide 222 and a defect indicator 224 coupled to the trajectory guide 222. The trajectory guide 222 may include one or more arm members 230 distributed about a periphery 232 of a guide body 226. Each of the arm members 230 may be independently movable relative to a longitudinal axis GA of the guide body 226 to set a trajectory of a guide member such as an elongated guide pin GP relative to tissue such as bone.

Referring to FIGS. 13-14, with continuing reference to FIG. 12, the defect indicator 224 may include a main body 236 integrally formed with, or otherwise coupled to, one of the arm members 230. The defect indicator 224 may include an indication member 238 configured to indicate a predetermined circumferential position about the longitudinal axis GA and/or longitudinal axis PA and/or a predetermined direction relative to the longitudinal axis GA and/or longitudinal axis PA. The predetermined direction may be associated with a position of a defect or abnormality along an articular surface of the bone. The indication member 238 may be integrally formed with, or otherwise coupled to, the main body 236.

The indication member 238 may include a pointer body 250 that tapers to an apex 254. The apex 254 may serve to establish an indicator 252 corresponding to the predetermined circumferential position and predetermined direction relative to the longitudinal axis GA. In implementations, the indication member 238 may include an indicator 252' established along the pointer body 250 (shown in dashed lines in FIG. 13 for illustrative purposes). The indicator 252' may extend along the apex 254 to indicate the predetermined circumferential position. The indication member 238 may be patient-specific such that the indicator 252, 252' may correspond to a single, predetermined circumferential position associated with a predetermined location of the patient anatomy. The predetermined circumferential position may be associated with a location of a bone defect or other abnormality of a patient, which may be determined preoperatively utilizing one or more images of the patient anatomy.

The indication member 238 may be releasable secured to the main body 236 of the defect indicator 224. The main body 236 may establish a recess 268 dimensioned to at least partially receive the indication member 238. The pointer body 250 may be at least partially insertable into the recess 268 such that the apex 254 is situated relative to the longitudinal axis GA to indicate a predetermined direction towards a defect or abnormality, as illustrated in FIGS. 12-13. The pointer body 250 may be at least partially insertable into the recess 268 such that the apex 254 is situated at the predetermined circumferential position relative to the longitudinal axis GA associated with the predetermined direction. The surgeon may form a first marking M1 along tissue such as bone to mark or otherwise specify the circumferential position of the indicator 252 relative to the longitudinal axis GA and/or longitudinal axis PA (M1 shown in FIGS. 12 and 15 for illustrative purposes).

Referring to FIG. 14, with continuing reference to FIGS. 12-13, the pointer body 250 may be movable in a third (e.g., radial) direction D3 such that the pointer body 250 is at least partially inserted into the recess 268. The indication member 238 may include one or more retention members 270 extending outwardly from the pointer body 250. The retention members 270 may be a pair of resiliently formed wings that are biased or movable inwardly in response to moving the retention members 270 into engagement with a wall of the main body 236 establishing a surface of the recess 268. The retention members 270 may include abutments 272 extending from an outer face of the retention members 270. The abutments 272 may be dimensioned to engage with surfaces of the main body 236 to limit movement of the indication member 238 relative to the main body 236 and capture the indication member 238 in the recess 268 at a fixed position.

The pointer body 250 may include various geometries or profiles to indicate the predetermined circumferential position associated with a location along the patient anatomy. In the implementation of FIG. 15, the indication member 252 may be substantially aligned with a reference plane REF extending radially from the longitudinal axis GA and through the pointer body 250. The surgeon may form the first marking M1 substantially along the reference plane REF to mark the circumferential position of the indicator 252 relative to the longitudinal axis GA and/or longitudinal axis PA.

In the implementation of FIG. 16, indication member 338 may include a pointer body 350 skewed relative to the reference plane REF to establish an angle α. An apex 354 of the pointer body 350 may be circumferentially offset from the reference plane REF relative to the longitudinal axis GA. The pointer body 350 may be dimensioned such that the apex 354 and associated indicator 352 may be skewed in a clockwise direction relative to the longitudinal axis GA, or may be skewed in a counterclockwise direction relative to the longitudinal axis GA as illustrated by the indication member 438 of FIG. 17.

Various techniques may be utilized to form the indication members 238, 338, 438 such as casting and three dimensional (3D) printing techniques. The main body 236 of the defect indicator 224 may be reusable, and the recess 268 may be dimensioned to receive indication members 238, 338, 438 of various shapes and sizes that may be specific to the anatomy of respective patients. The techniques disclosed herein may provide the surgeon flexibility in selection of indication members that are tailored to a particular patient, which may improve precision in identifying an area of maximum bone loss or erosion for subsequent removal.

Figure 18:
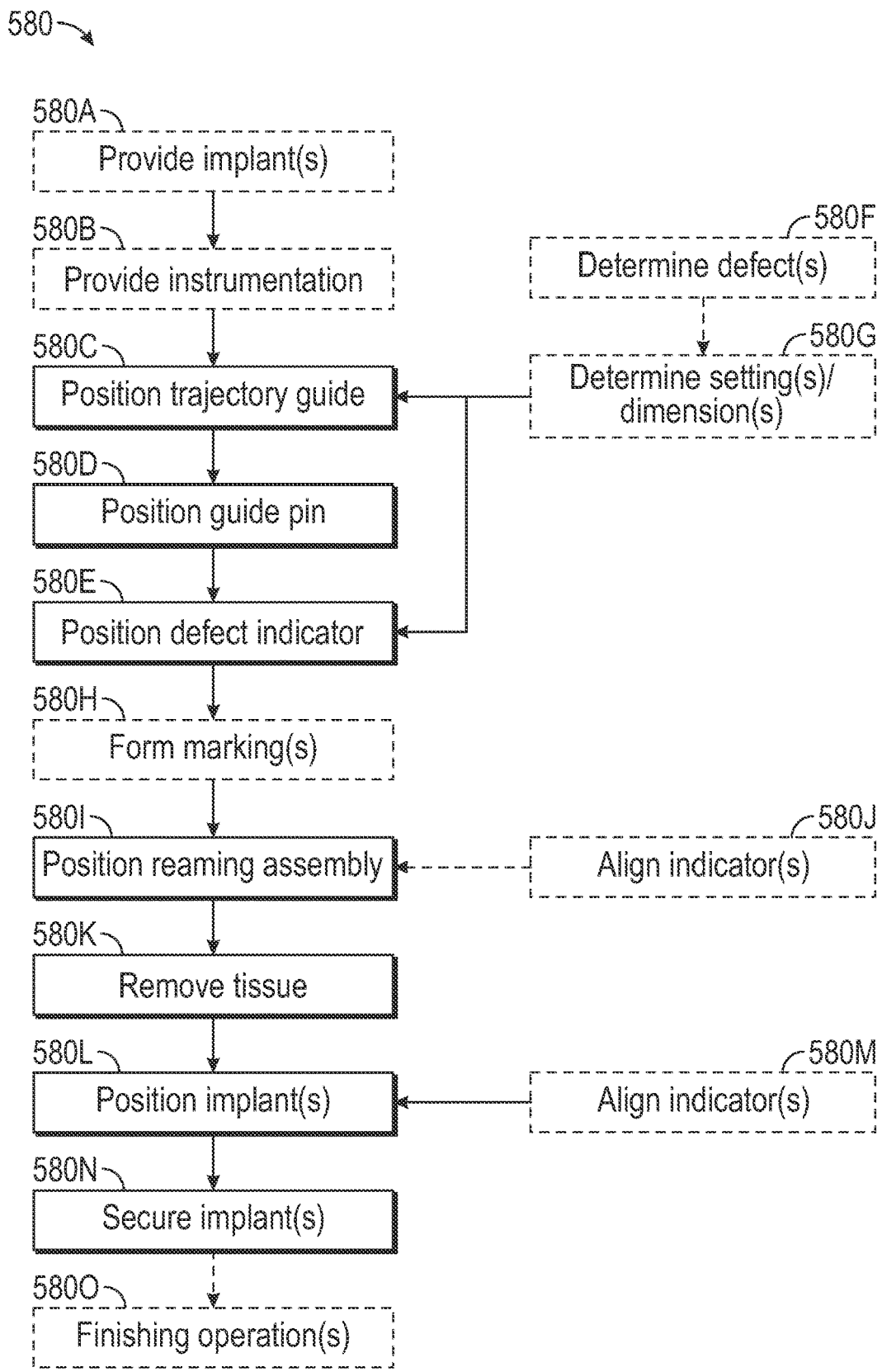
FIG. 18 illustrates a method of installing an orthopaedic implant.

Referring to FIG. 18, a method of installing an orthopaedic implant in a flowchart 580 is disclosed. The method 580 may be utilized to perform an arthroplasty for restoring functionality to shoulders, knees, hips and other joints having advanced cartilage disease, for example. The method 580 may be utilized with any of the instrumentation and orthopedic implants disclosed herein, including the trajectory assemblies 20, 120, 220, trajectory guides 22, 122, 222, defect indicators 24, 124, 224 and/or indication members 38, 138, 238, 338, 448. The method 580 may be utilized to indicate a location along a patient anatomy, such as a predetermined or selected circumferential position of a bone defect or abnormality associated with the location. Fewer or additional steps than are recited below could be performed within the scope of this disclosure, and the recited order of steps is not intended to limit this disclosure.

Figure 19:
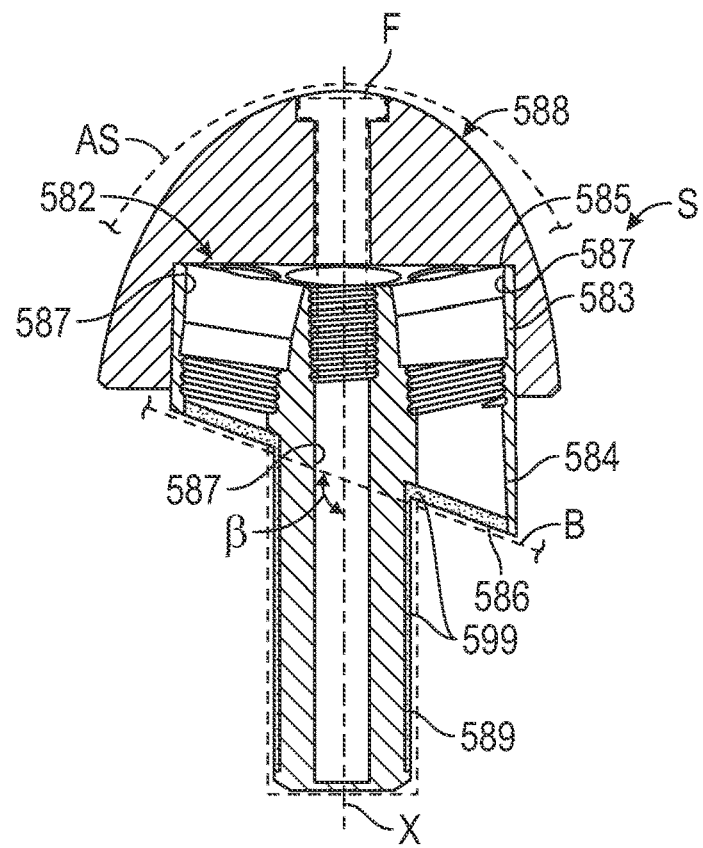
FIG. 19 illustrates a sectional view of an implant situated relative to a surgical site.
Figure 20:
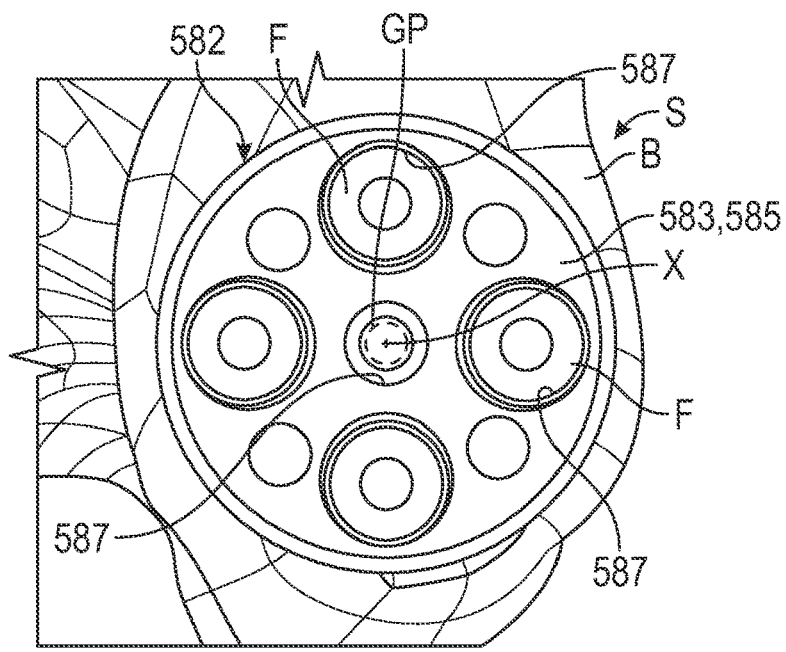
FIG. 20 illustrates a plan view of the implant of FIG. 19.

At step 580A, one or more orthopaedic implants may be provided to the surgeon. An exemplary implant 582 is illustrated in FIGS. 19-20. The implant 582 may be positioned along and dimensioned to abut bone B or other tissue along a surgical site S. The implant 582 may be configured to interface with an articular surface AS of an adjacent bone or adjacent implant to restore functionality to the joint (articular surface AS shown in dashed lines in FIG. 19 for illustrative purposes).

The implant 582 may have various configurations and geometries, which may be patient or non-patient specific. Referring to FIG. 19, with continuing reference to FIG. 18, the implant 582 may include a main body portion 583 and an augment portion 584 that cooperate to establish a front (e.g., first) face 585 and a rear (e.g., second) face 586 of the implant 582. The implant 582 may extend along an implant axis X. The rear face 586 may be dimensioned to abut or contact a surface of the bone B or other tissue along the surgical site S (bone B shown in dashed lines in FIG. 19 for illustrative purposes). The implant 582 may include an anchoring stem (e.g., member) 589 extending outwardly from the rear face 586. The anchoring stem 589 may have a generally cylindrical geometry and may be dimensioned to extend along the implant axis X. The implant 582 may include one or more coatings 599 disposed along surfaces of the implant 582. The coatings 599 may promote bone ingrowth and fixation of the implant 582 to the adjacent bone B.

The augment portion 584 may have various geometries to cooperate with the adjacent bone B. The augment portion 584 may have a generally wedge-shaped profile. The implant 582 may be dimensioned such that the rear face 586 is established at an oblique angle β relative to the implant axis X. In other implementations, the rear face 586 is substantially parallel to the front face 585.

The implant 582 may include one or more apertures (e.g., passages) 587. Each aperture 587 may extend at least partially or completely through the main body portion 583 and/or augment portion 584 between the front face 585 and rear face 586. Each aperture 587 may be dimensioned to receive a respective fastener F (Figure Each fastener F may be at least partially inserted into a respective one of the apertures 587. Fasteners F may include compression screws configured to secure the implant 582 to the bone B.

The implant 582 may be coupled to an articulation member 588. The articulation member 588 may include an articulating surface having a generally concave or convex shaped profile to cooperate with the articulate surface AS of the adjacent bone or implant. One of the fasteners F may be utilized to fasten or otherwise secure the articulation member 548 to the front face 585 of the implant 582. The fasteners F may be secured to the implant 582 utilizing a threaded connection. At least one of the apertures 587 may be dimensioned to receive a guide member, such as a guide pin GP (illustrated in dashed lines in FIG. 20). In other implementations, the implant 582 may provide the articulating surface.

The surgeon may be provided with various instrumentation at step 580B. The instrumentation may include a trajectory assembly 520 (FIG. 21) and/or a reaming assembly 590 (FIG. 22). Implants 582 of various shapes and/or sizes and instrumentation including the trajectory assembly 520 and/or reaming assembly 590 may be provided to the surgeon as a kit for performing an arthroplasty. Other components and devices may be provided in the kit such as one or more guide members including the guide pin GP and/or fasteners F.

Figure 21:
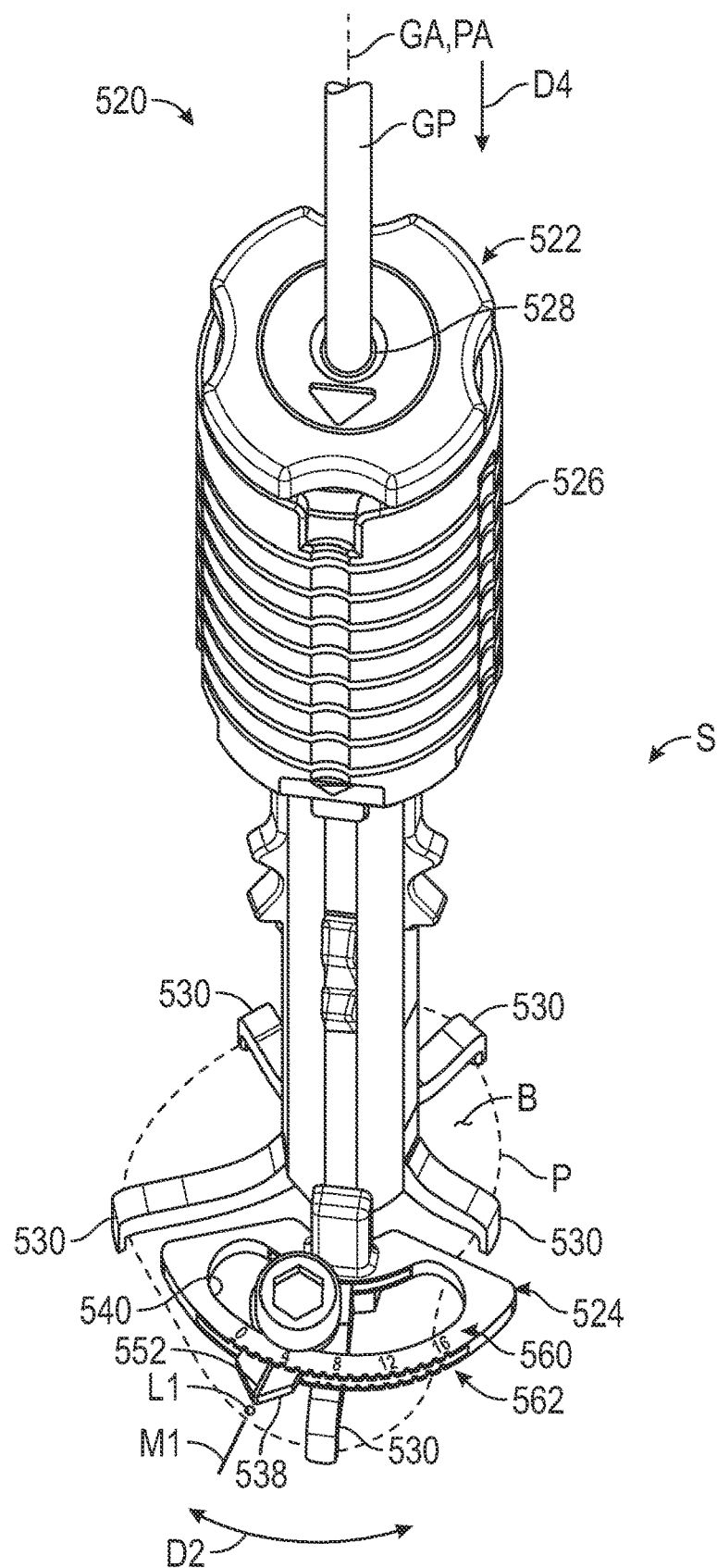
FIG. 21 illustrates a perspective view of an exemplary trajectory assembly situated relative to a surgical site.
Figure 22:
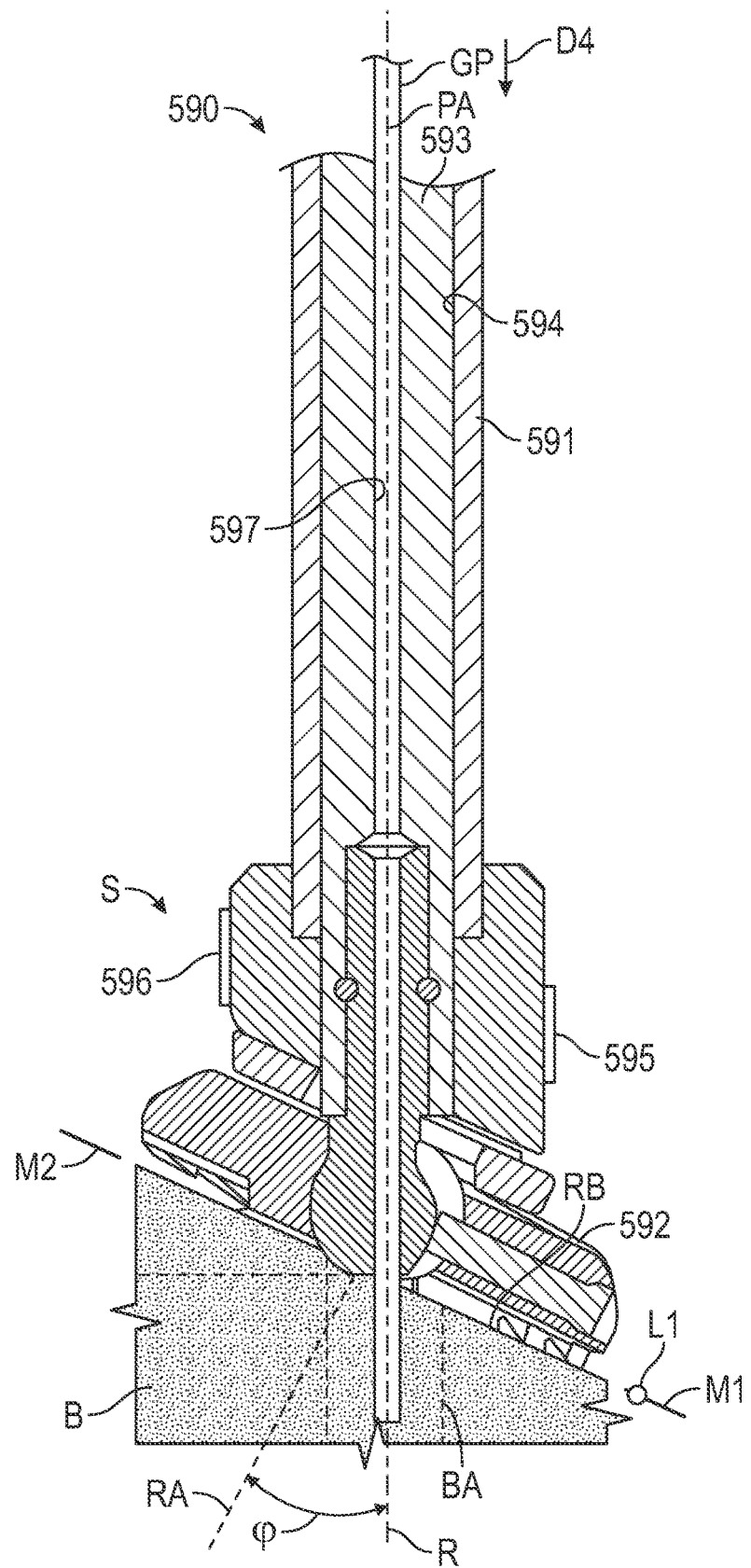
FIG. 22 illustrates a sectional view of a reaming assembly situated relative to the surgical site.

Referring to FIG. 21, with continuing reference to FIG. 18, a trajectory guide 522 of the trajectory assembly 520 may be positioned relative to the surgical site S at step 580C. Step 580C may include positioning the trajectory guide 522 in abutment with the bone B according to a predetermined trajectory. The predetermined trajectory may include a predetermined location a corresponding to a point of insertion of the guide pin GP along an articular surface of the bone B and/or a predetermined orientation of an axis of the guide pin GP extending through the predetermined location. The predetermined trajectory may be established utilizing any of the techniques disclosed herein. Positioning the trajectory guide 522 at step 580C may include moving and/or otherwise positioning one or more arm members 530 relative to a guide body 526 and/or longitudinal axis GA of the trajectory guide 522. Step 580C may include moving the arm members 530 to respective positions relative to the guide body 526 and into abutment with the bone B to establish the predetermined trajectory. The arm members 530 may be moved to respective positions relative to the longitudinal axis GA of the trajectory guide 522 prior to, during and/or subsequent to positioning the trajectory guide 522 into abutment with the bone B. The arm members 530 may be positioned in contact or abutment with a periphery P of the articular surface of the bone B (periphery P shown in dashed lines for illustrative purposes). The periphery P may be established by a glenoid rim of a glenoid.

At step 580D, one or more guide pins GP may be positioned in the bone B according to the predetermined trajectory established by the trajectory guide 522. Step 580D may include moving the guide pin GP in a fourth (e.g., axial) direction D4 along the longitudinal axis GA of the trajectory guide 522. The guide pin GP may be at least partially inserted into and through a passageway 528 of the guide body 526.

At step 580E, a defect indicator 524 may be positioned to indicate a predetermined or specified location L1 along the patient anatomy, such as a bone defect or another abnormality. The defect indicator 524 may be carried by a selected one of arm members 530 of the trajectory guide 522. The defect indicator 524 may be fixedly attached, releasably secured, or otherwise coupled to the trajectory guide 522 utilizing any of the techniques disclosed herein. The defect indicator 524 may be positioned relative to the trajectory guide 522 to indicate the direction and/or circumferential position of the indicator 552 relative to the longitudinal axis GA and/or longitudinal axis PA. The circumferential position may be substantially circumferentially aligned with the predetermined location L1 along the patient anatomy. The direction of the indicator 552 may point towards the predetermined location L1 to provide the surgeon or assistant a visual indication of the position of the defect or abnormality.

Various techniques may be utilized to position the trajectory guide 522 at step 580C and/or position the defect indicator 524 at step 580E. For example, one or more defects or abnormalities may be determined at 580F. One or more of the defects or abnormalities may correspond to a localized area or region of maximum bone loss or erosion along the bone B at the surgical site S. Step 580F may include determining the location L1 of the localized area or region of maximum bone loss or erosion. Various techniques may be utilized to determine the localized region of maximum bone loss or erosion, such as determining bone densities and/or surface contouring in one or more images or models of the bone B.

At step 580G, one or more settings and/or dimensions may be determined to position or otherwise configure the trajectory guide 522 at step 580C and/or position or otherwise configure the defect indicator 524 at step 580E. The settings and dimensions may include positions of the arm members 530 relative to the guide body 526 and/or longitudinal axis GA. The settings may be specified in a preoperative plan and transferred to the trajectory guide 522 and/or defect indicator 524. The arm members 530 may be locked or otherwise fixed at respective positions relative to the guide body 526 and/or longitudinal axis GA of the trajectory guide 522, with the respective positions corresponding to the setting(s) and/or dimension(s).

Step 580G may include determining one or more settings of the defect indicator 524. Step 580G may include identifying a selected one of the arm members 530 to position or couple the defect indicator 524 onto. Step 580E may include positioning the defect indicator 524 on the selected arm member 530 according to the specified setting.

Step 580G may include determining position of the indicator 552 relative to the ruler 560 corresponding to the predetermined or selected circumferential position relative to the longitudinal axis GA and/or longitudinal axis PA. The predetermined circumferential position may correspond to a position of the determined defect or abnormality at step 580F. The predetermined circumferential position may correspond to a position of maximum bone defect or erosion along an articular surface of the joint. A position of the indicator 552 relative to the indicia 562 along the ruler 560 may correspond to an area of maximum bone loss or erosion at or otherwise adjacent to the predetermined location L1 along the bone B.

Step 580E may include moving the indication member 538 relative to the trajectory guide 522, including moving the indication member 538 relative to the respective arm member 530 carrying the defect indicator 524. Step 580E may include moving the indication member 538 relative to the trajectory guide 522 in a direction D2 about the longitudinal axis GA of the trajectory guide 522 and/or the longitudinal axis PA of the guide pin GP from a first position to a second position to indicate the selected direction and/or circumferential position of the indicator 552. Step 480E may include moving the indication member 538 in the direction D2 along the first arcuate slot 540 to set the circumferential position of the indicator 552 relative to the ruler 560. The indicator 552 may point in a direction towards the location L1 associated with the determined area of maximum bone loss or erosion.

At step 580H, one or more markings may be formed along a surface of the bone B or another surface along the surgical site S. For example, step 580H may include forming a first marking M1 along the bone B according to the direction and/or circumferential position indicated by the indicator 552 of the defect indicator 524. Step 580H may occur such that the first marking M1 may be substantially aligned with the direction and/or circumferential position indicated by the indicator 552 relative to the longitudinal axis GA of the trajectory guide 522 and/or the longitudinal axis PA of the guide pin GP (see also FIGS. 23 and 25).

Figure 24:
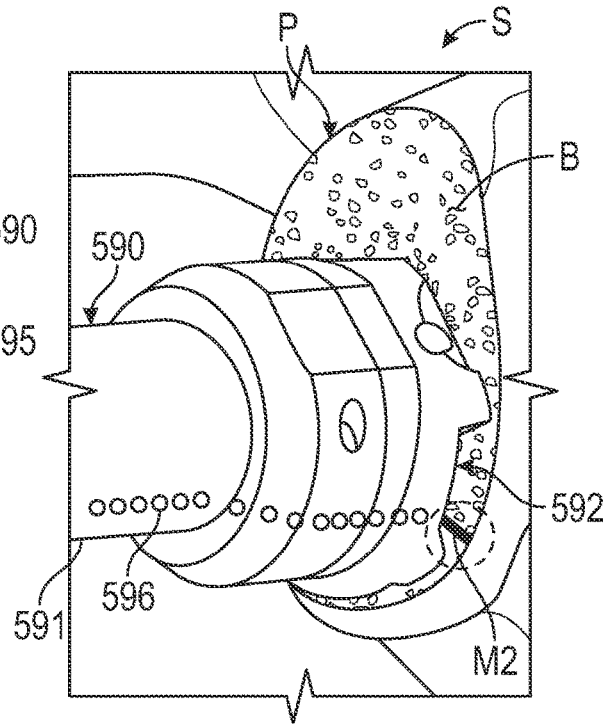
FIG. 24 illustrates another perspective view of the reaming assembly situated relative to the surgical site.
Figure 25:
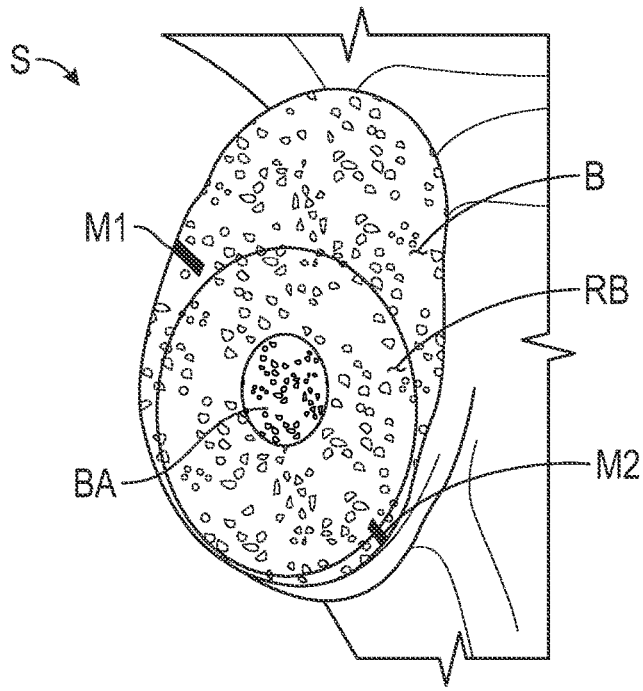
FIG. 25 illustrates the reaming assembly of FIGS. 22-24 removed from the surgical site.

Step 580H may include forming a second marking M2 along the surface of the bone B or another surface of the surgical site S. The second marking M2 may be formed approximately 180 degrees offset from the first marking M1, as illustrated in FIGS. 22 and 24-25. The second marking M2 may be formed by repositioning the defect indicator 524 onto another one of the arm members 530 than the arm member 530 associated with the first marking M1. The position of the indicator 552 relative to the ruler 560 associated with the second marking M2 may be same or may differ from the position of the indicator 552 associated with the first marking M1. The trajectory assembly 520 may be removed from the guide pin GP and from the surgical site S subsequent to indicating the circumferential position including forming the markings M1 and/or M2. The markings M1, M2 may be formed with a pen or marker, for example. Forming the markings M1 and/or M2 may facilitate positioning of the reaming assembly 590 and/or implant 582.

Referring to FIG. 22, with continuing reference to FIG. 18, the reaming assembly 590 may be positioned along the surgical site S at step 580I. Step 580I may include positioning the reaming assembly 590 along the guide pin GP. Step 580I may include moving the reaming assembly 590 in the direction D4 along the longitudinal axis PA of the guide pin GP and into abutment with a surface of the bone B.

The reaming assembly 590 may include a housing 591 and a reaming head 592 coupled to the housing 591. The reaming head 592 may be coupled to a drive shaft 593. The housing 591 and drive shaft 593 may be dimensioned to extend along a longitudinal (e.g., assembly) axis R of the reaming assembly 590. The reaming head 592 may be rotatable about a reaming axis RA. The reaming axis RA may be substantially parallel or oblique to the longitudinal axis R of the reaming assembly 590. The housing 591 may be configured to at least partially receive the guide pin GP to set an orientation of the housing 591 relative to the surgical site S. The housing 591 may include a passageway 594 dimensioned to at least partially receive the drive shaft 593. The drive shaft 593 may be coupled to tooling to cause the reaming head 592 to rotate about the reaming axis RA.

The drive shaft 593 may include a passageway 597 that at least partially receives the guide pin GP. The reaming assembly 590 may be configured such that the reaming head 592 and associated reaming axis RA may be inclined or oriented at an oblique angle φ relative to the longitudinal axis PA of the guide pin GP and the longitudinal axis R of the reaming assembly 590. The reaming assembly 590 may be rotatable or otherwise moveable such that a distalmost position of the reaming head 592 may be substantially oriented in the predetermined or selected direction specified by the indicator 552 relative to the longitudinal axis PA and/or longitudinal axis GA. The reaming assembly 590 may be rotatable or otherwise moveable such that the distalmost position of the reaming head 592 is substantially aligned with the predetermined or selected circumferential position about the longitudinal axis PA corresponding to the direction specified by the indicator 552. The direction of the indicator 552 associated with the circumferential position about the longitudinal axis GA and/or longitudinal axis PA may be indicated or specified with one or more markings M1, M2 at step 580E. The reaming head 592 may be oriented at the oblique angle φ such that the distalmost position of the reaming head 592 is substantially aligned with the first marking M1 and the associated circumferential position relative to the longitudinal axis PA of the guide pin GP.

Figure 23:
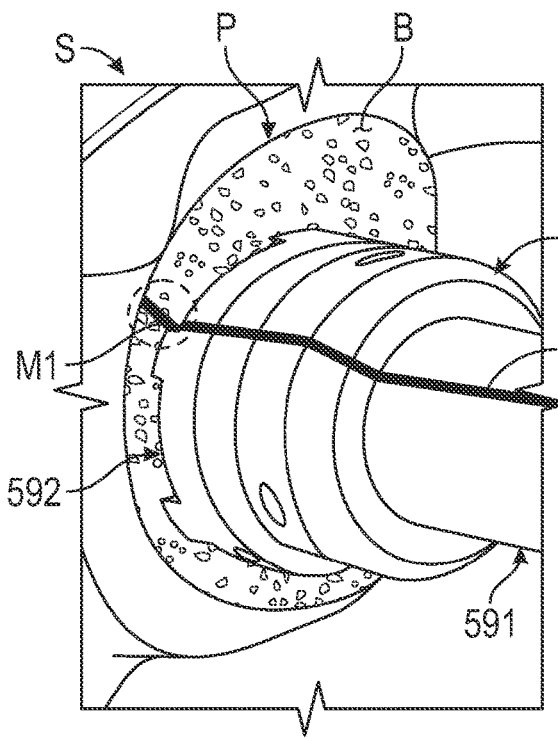
FIG. 23 illustrates a perspective view of the reaming assembly situated relative to the surgical site.

The reaming assembly 590 may include one or more indicators to facilitate positioning of the reaming head 592 relative to the predetermined location L1. In implementations, the reaming assembly 590 may include a first indicator 595 and a second indicator 596. The first indicator 595 and second indicator 596 may be established along a perimeter of the housing 591, a perimeter of reaming head 592 and/or another portion of the reaming assembly 590, as illustrated in FIGS. 23-24. The first and second indicators 595, 596 are illustrated schematically along the housing 591 in FIG. 22. The first and second indicators 595, 596 may be circumferential offset by about 180 degrees from each other relative to the longitudinal axis R of the reaming assembly 590 (FIG. 22). In implementations, one of the first and second indicators 595, 596 may be omitted.

Positioning the reaming assembly at step 580I may include substantially aligning one or more of the indicators 595, 596 along the reaming assembly 590 with one or more of the markings M1 and/or M2. Step 580J may include substantially aligning the indicator 595 with the first marking M1 along a surface of the bone B such that the indicator 595 may be associated with the distalmost position of the reaming head 592 relative to the longitudinal axis R of the reaming assembly 590 and/or the longitudinal axis PA of the guide pin GP, as illustrated in FIGS. 22-23. Step 580J may include substantially aligning the second indicator 596 with the second marking M2 along the bone B such that the second indicator M2 may be associated with a proximalmost position of the reaming head 592, as illustrated in FIGS. 22 and 24. The first indicator 595 (or the second indicator 596) may be substantially positioned in the predetermined or specified direction of the indictor 552 and may be substantially aligned with the determined circumferential position about the longitudinal axis PA in response to rotation of the housing 591 about the guide pin GP. The indicator(s) 595, 596 may be utilized to precisely indicate a direction and/or the location L1 associated with an area of maximum bone defect or erosion for a subsequent reaming operation.

Figure 26:
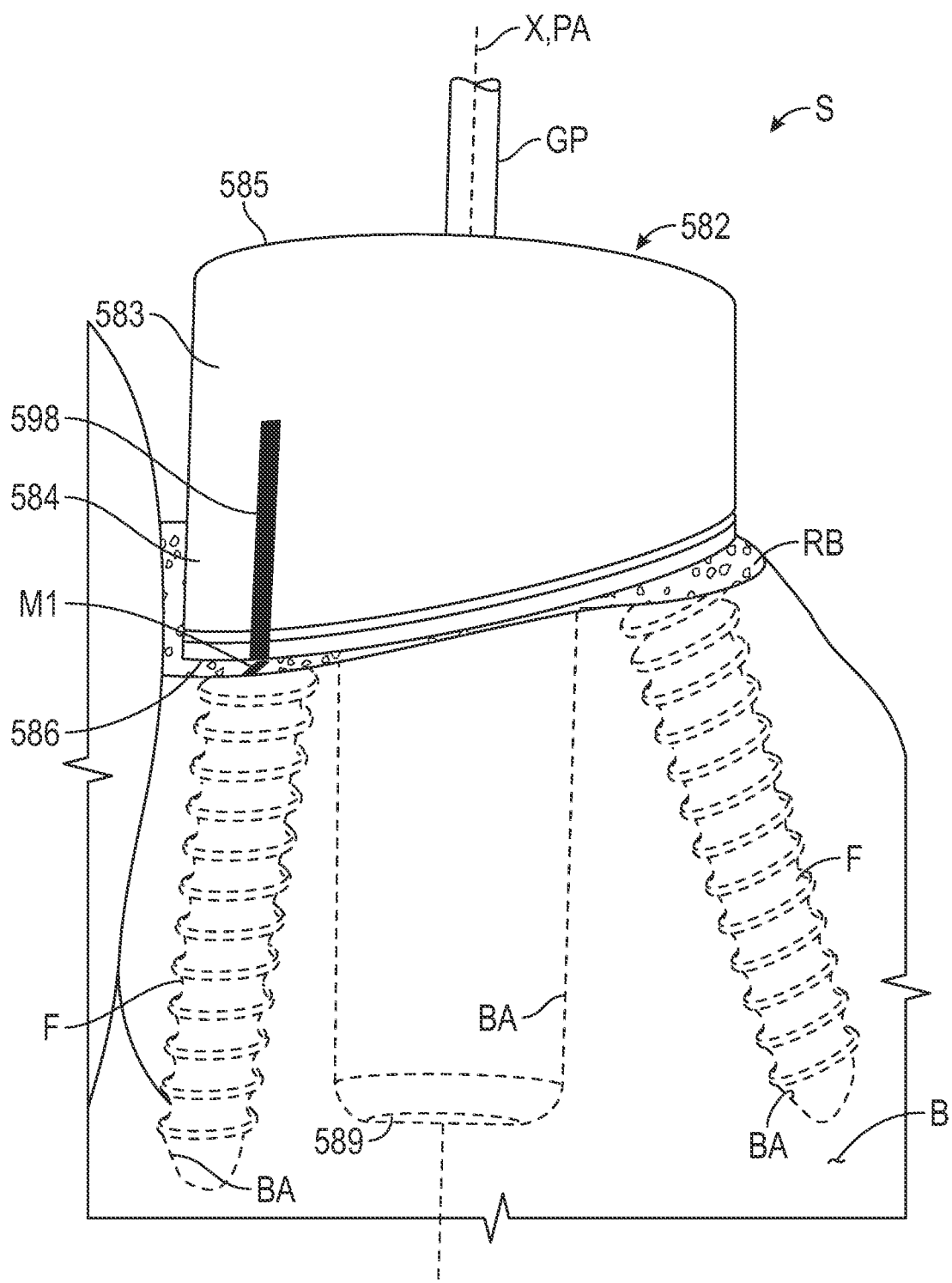
FIG. 26 illustrates the implant of FIGS. 19-20 situated relative to the surgical site.

Referring to FIGS. 23-25, with continuing reference to FIGS. 18 and 22, tissue such as bone B may be removed from the surgical site S at step 580K. Step 580K may include rotating the reaming head 592 about the reaming axis RA and about the guide pin GP to remove a portion of the bone B. The reaming head 592 may be utilized to form an angled cut along an articular surface of the bone B at the oblique angle cp. Step 580K may include removing the portion of the bone B from a glenoid of a patient. Thereafter, the reaming assembly 590 may be removed from the surgical site S to provide access to the reamed bone RB, as illustrated in FIG. 25. Step 580K may include forming one or more apertures BA along the reamed bone RB (FIGS. 25-26). The apertures BA may be formed utilizing various techniques, such as a drilling or milling operation.

Referring to FIG. 26, with continuing reference to FIG. 18, one or more implants 582 may be positioned along the surgical site S at step 580L. Step 580L may include positioning the implant 582 along the reamed bone RB subsequent to removing a portion of the bone B or tissue at step 580K. Positioning the implant 582 may include positioning the anchoring stem 589 in one of the apertures BA.

The implant 582 may include an indicator 598 established along a periphery of the augment portion 584 and/or another portion of the implant 582 to facilitate placement. Step 580L may include substantially aligning the indicator 598 with the first marking M1 (or the second marking M2) along the bone B. The rear face 586 may be dimensioned to abut the reamed bone RB at a predetermined location and orientation of the implant 582, which may be determined preoperatively.

At step 580N, the implant(s) 582 may be fixedly attached or otherwise secured to the bone B along the surgical site S at the determined location and orientation of the implant 582 established at step 580M. Step 580N may include fixedly attaching the implant 582 to the bone B with one or more fasteners F.

One or more finishing operations may be performed at step 580O. Exemplary finishing operations may include closing an incision at the surgical site S.

The novel devices and methods of this disclosure provide versatility in dimensioning or shaping a recess at a surgical site. The disclosed trajectory assemblies, including the disclosed defect indicators, may provide a means for indicating a precise location of a defect along and/or adjacent to an articular surface of joint, such as the articular surface of a glenoid. The precise location may be patient-specific and may be determined based on a preoperative plan tailored to the particular patient. The determined location information may be transferred to the defect indicator in the form of one or more dimensions or settings. The disclosed defect indicators may be utilized to precisely identify a circumferential position associated with the determined location, which may be utilized to orient the distalmost position of the reaming head of the reaming assembly, and which may be utilized to orient a respective implant. At least a portion of the bone defect or abnormality may be reamed by the reaming head at an angle relative to the guide pin based on the specified circumferential position, which may preserve a relatively greater amount of healthy bone and may lead to improved healing at the surgical site.

Although the different non-limiting embodiments are illustrated as having specific components or steps, the embodiments of this disclosure are not limited to those particular combinations. It is possible to use some of the components or features from any of the non-limiting embodiments in combination with features or components from any of the other non-limiting embodiments.

It should be understood that like reference numerals identify corresponding or similar elements throughout the several drawings. It should further be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. An assembly for preparation of a surgical site comprising:
a trajectory guide including a guide body extending in an axial direction along a guide axis between a proximal end and a distal end and including a plurality of arm members slidably coupled to and distributed about a periphery of the guide body, the plurality of arm members including a set of arm members dimensioned to abut bone, each of the arm members including a respective first portion coupled to the guide body and a respective second portion extending laterally from the first portion, the guide body having a passageway extending along a longitudinal axis, the passageway extending a distance between the proximal end and the distal end of the guide body, the passageway dimensioned to at least partially receive a guide pin to set a trajectory of the guide pin relative to bone, and each of the arm members slidably moveable in the axial direction relative to the guide axis of the guide body; and a defect indicator coupled to one of the arm members such that the defect indicator is moveable in the axial direction together with the respective arm member relative to the guide body, the defect indicator including a main body and a patient-specific indication member including a pointer body extending from the main body, the indication member dimensioned to indicate a direction relative to the longitudinal axis that corresponds to a predetermined position of a bone defect of a patient.

2. The assembly as recited in claim 1, wherein:
the pointer body tapers to an apex dimensioned to point in the direction.

3. The assembly as recited in claim 1, wherein:
each arm member of the set of arm members is moveable relative to the guide body to set the trajectory of the guide pin in response to abutment with bone.

4. The assembly as recited in claim 3, wherein each arm member of the set of arm members includes a third portion, the second portion extends laterally between the first portion and the third portion, and the third portion establishes a terminal end dimensioned to abut bone.

5. The assembly as recited in claim 1, wherein the indication member is integrally formed with the main body of the defect indicator.

6. The assembly as recited in claim 1, wherein the indication member is releasably secured to the main body of the defect indicator.

7. The assembly as recited in claim 6, wherein the main body is integrally formed with the respective arm member.

8. The assembly as recited in claim 6, wherein: the main body establishes a recess;
the pointer body that tapers to an apex; and
the pointer body is at least partially insertable into the recess such that the apex is situated relative to the longitudinal axis to indicate the direction.

9. The assembly as recited in claim 8, wherein:
the indication member includes one or more retention members extending outwardly from the pointer body.

10. The assembly as recited in claim 9, wherein:
the one or more retention members include a pair of resiliently formed wings that are biased in response to moving the wings into engagement with a wall of the main body that establishes the recess.

11. The assembly as recited in claim 10, wherein:
each of the wings includes an abutment extending from an outer face of the respective wing, and the abutment is dimensioned to engage with the main body to limit movement of the indication member relative to the main body.

12. The assembly as recited in claim 11, wherein:
the abutments of the wings cooperate with the main body to capture the indication member in the recess.

13. The assembly as recited in claim 8, wherein the defect indicator is dimensioned such that the apex of the indication member is substantially aligned along a reference plane in response to securing the indication member in the recess, and the reference plane extends radially from the longitudinal axis and through the pointer body.

14. The assembly as recited in claim 8, wherein the defect indicator is dimensioned such that the apex of the indication member is offset from a reference plane in response to securing the indication member in the recess, and the reference plane extends radially from the longitudinal axis and through the pointer body.

15. The assembly as recited in claim 1, wherein the indication member includes an apex and an indicator, the apex is dimensioned to face away from the guide body, and the indicator is dimensioned to extend along the apex to indicate the direction.

16. The assembly as recited in claim 1, wherein the main body is secured to a distal end of the respective arm member.

17. The assembly as recited in claim 1, wherein the bone is a glenoid.

18. A kit for arthroplasty comprising:
an orthopaedic implant dimensioned to abut bone along a surgical site; a trajectory assembly comprising:
a trajectory guide including a guide body extending in an axial direction along a guide axis between a proximal end and a distal end and including a plurality of arm members slidably coupled to and distributed about a periphery of the guide body, each of the arm members including a respective first portion coupled to the guide body and a respective second portion extending laterally from the first portion, the guide body having a passageway extending along a longitudinal axis, the passageway extending a distance between the proximal end and the distal end of the guide body, the passageway dimensioned to at least partially receive a guide pin to set a trajectory of the guide pin relative to bone, and each of the arm members slidably moveable in the axial direction relative to the guide axis of the guide body; and
a defect indicator coupled to one of the arm members such that the defect indicator is moveable in the axial direction together with the respective arm member relative to the guide body, the defect indicator including a main body and a patient-specific indication member including a pointer body extending from the main body and configured to indicate a direction relative to the guide pin that corresponds to a predetermined position of a bone defect of a patient; and
a reaming assembly comprising:
a housing configured to at least partially receive the guide pin to set an orientation of the housing relative to the surgical site; and
a reaming head rotatable about a reaming axis to remove bone, wherein the reaming axis is oriented at an oblique angle relative to the
assembly axis, and the reaming assembly is moveable such that a distalmost position of the reaming head is substantially positioned in the direction.

19. The kit as recited in claim 18, wherein the indication member is releasably secured to the main body of the defect indicator.

20. The kit as recited in claim 18, wherein:
the reaming assembly includes an indicator substantially aligned with the distalmost position of the reaming head relative to the assembly axis; and
the housing is rotatable about the guide pin such that the indicator is substantially positioned in the direction.

* * * * *